United States Patent
Ishida et al.

(10) Patent No.: US 11,461,884 B2
(45) Date of Patent: Oct. 4, 2022

(54) FIELD MANAGEMENT APPARATUS, FIELD MANAGEMENT METHOD, AND COMPUTER READABLE RECORDING MEDIUM

(71) Applicant: NEC Corporation, Tokyo (JP)

(72) Inventors: Kousuke Ishida, Tokyo (JP); Hajime Ishikawa, Tokyo (JP); Shinji Oominato, Tokyo (JP); Shunsuke Akimoto, Tokyo (JP); Shintaro Matsumoto, Tokyo (JP); Masami Sakaguchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 281 days.

(21) Appl. No.: 16/496,644

(22) PCT Filed: Mar. 23, 2018

(86) PCT No.: PCT/JP2018/011828
§ 371 (c)(1),
(2) Date: Sep. 23, 2019

(87) PCT Pub. No.: WO2018/181041
PCT Pub. Date: Oct. 4, 2018

(65) Prior Publication Data
US 2020/0380663 A1 Dec. 3, 2020

(30) Foreign Application Priority Data

Mar. 29, 2017 (JP) .............................. JP2017-066190

(51) Int. Cl.
*G06T 7/00* (2017.01)
*G06T 7/73* (2017.01)
(Continued)

(52) U.S. Cl.
CPC ............ *G06T 7/0004* (2013.01); *A01G 25/00* (2013.01); *G01M 3/38* (2013.01); *G01N 33/246* (2013.01);
(Continued)

(58) Field of Classification Search
None
See application file for complete search history.

(56) References Cited

U.S. PATENT DOCUMENTS

2014/0072209 A1\* 3/2014 Brumby ............... G06K 9/6244
382/160
2015/0254800 A1 9/2015 Johnson et al.
(Continued)

FOREIGN PATENT DOCUMENTS

EP 3046066 A1 7/2016
JP 2005-085059 A 3/2005
(Continued)

OTHER PUBLICATIONS

Agarap AF. An architecture combining convolutional neural network (CNN) and support vector machine (SVM) for image classification. arXiv preprint arXiv:1712.03541. Dec. 10, 2017. (Year: 2017).\*
(Continued)

*Primary Examiner* — Emily C Terrell
*Assistant Examiner* — Nathan J Bloom

(57) ABSTRACT

A field management apparatus 10 is provided with a learning model generation unit 11 that generates a learning model 15, to learn feature amounts of the image of the phenomenon that results from the fault in the field equipment, an image acquisition unit 12 that acquires an aerial image of a target region, an image specification unit 13 that applies the aerial image to the learning model 15, and specifies an image of the phenomenon that results from the fault in the field equipment in the aerial image, and a fault location specification
(Continued)

unit 14 that specifies a fault location of the field equipment in the target region, based on the image of the phenomenon that results from the fault in the field equipment.

15 Claims, 17 Drawing Sheets

(51) Int. Cl.
| | |
|---|---|
| *G06N 20/00* | (2019.01) |
| *A01G 25/00* | (2006.01) |
| *G01M 3/38* | (2006.01) |
| *G01N 33/24* | (2006.01) |
| *G06Q 50/02* | (2012.01) |
| *G06V 20/10* | (2022.01) |

(52) U.S. Cl.
CPC .............. *G06N 20/00* (2019.01); *G06Q 50/02* (2013.01); *G06T 7/0002* (2013.01); *G06T 7/75* (2017.01); *G06V 20/188* (2022.01); *G06T 2207/10032* (2013.01); *G06T 2207/10044* (2013.01); *G06T 2207/20081* (2013.01); *G06T 2207/20084* (2013.01); *G06T 2207/30188* (2013.01)

(56) References Cited

U.S. PATENT DOCUMENTS

| | | | |
|---|---|---|---|
| 2016/0093212 A1 | 3/2016 | Barfield, Jr. et al. | |
| 2016/0169855 A1* | 6/2016 | Baity | G01N 33/24 47/58.1 SC |
| 2016/0202227 A1 | 7/2016 | Mathur et al. | |
| 2017/0083747 A1* | 3/2017 | Guan | G06K 9/0063 |
| 2018/0164179 A1* | 6/2018 | Bagasra | B64C 39/024 |
| 2018/0189564 A1* | 7/2018 | Freitag | A01G 22/00 |
| 2018/0239991 A1* | 8/2018 | Weller | G06V 20/188 |
| 2018/0247416 A1* | 8/2018 | Ruda | G06T 7/0004 |
| 2018/0373932 A1* | 12/2018 | Albrecht | G06F 17/14 |
| 2020/0134384 A1* | 4/2020 | Hino | G06K 9/6271 |
| 2020/0175352 A1* | 6/2020 | Cha | G06N 3/0454 |

FOREIGN PATENT DOCUMENTS

| | | |
|---|---|---|
| JP | 2007-156568 A | 6/2007 |
| JP | 2012-164109 A | 8/2012 |
| JP | 2013-210207 A | 10/2013 |

OTHER PUBLICATIONS

Srdjan Sladojevic et al. "Deep Neural Networks Based Recognition of Plant Diseases by Leaf Image Classification", Computational Intelligence and Neuroscience, May 29, 2016, XP055385550, pp. 1-11 (11 pages).

Extended European Search Report issued in European Patent Application No. 18776388.3, dated Jan. 3, 2020, 8 pages.

International Search Report corresponding to PCT/JP2018/011828 dated Jun. 19, 2018 (2 pages).

Yokoya, Naoto et al., Hyperspectral Image Processing for Advanced Earth Observation, Journal of the Japanese Society for Artificial Intelligence, Jul. 1, 2014, vol. 29, No. 4, pp. 357-365, ISSN 2188-2266 (11 pages).

* cited by examiner

Fig.15

|   | (1) | (2) | (3) | (4) | (5) | (6) | · · · · · |
|---|---|---|---|---|---|---|---|
| 1 | | | | | | | |
| 2 | | | | | | | |
| 3 | | | ● | | | | |
| 4 | | | | | | | |
| 5 | | | | | | | |
| 6 | | | | | | | |
| ⋮ | | | | | | | |

● SOIL MOISTURE SENSOR

FIELD MANAGEMENT APPARATUS, FIELD MANAGEMENT METHOD, AND COMPUTER READABLE RECORDING MEDIUM

CROSS REFERENCE-TO RELATED APPLICATIONS

This application is a national stage application of International Application No. PCT/JP2018/011828 entitled "Field Management Apparatus, Field Management Method, and Computer Readable Recording Medium" filed on Mar. 23, 2018, which claims priority to Japanese Patent Application No. 2017-066190 filed on Mar. 29, 2017, the disclosures of which are hereby incorporated by reference in their entirety.

TECHNICAL FIELD

The present invention relates to a field management apparatus and a field management method that are for managing a field, and, furthermore, to a computer readable recording medium that has a program for realizing the apparatus and method recorded thereon.

BACKGROUND ART

In recent years, in the agricultural field, efforts to support producers have been made by utilizing IT technology. For example, Patent Document 1 discloses an agricultural system for collecting various data, using a camera, a multispectral sensor, a sap flow sensor, a temperature sensor, a soil temperature sensor that are installed in a field, an unmanned aircraft that collects image data, and the like.

The agricultural system disclosed in Patent Document 1 supports a producer by applying the various data that is collected to a learning model and specifying action that the producer should take. For example, the agricultural system disclosed in Patent Document 1 is able to give a warning to the producer to do maintenance within a few days in the case where there is a problem with irrigation equipment, based on collected data. The producer can thereby become aware of the fault in the irrigation equipment, and is able to manage the field in a stable manner.

Patent Document 2 also discloses a system that supports producers, based on sensor data output by various sensors installed in the field. However, with the system disclosed in Patent Document 2, given the difficulty of judging whether or not an anomaly has occurred simply by collecting sensor data, attributes are prescribed depending on the installation position, and the various sensors are classified by the respective attributes. The system disclosed in Patent Document 2 then detects anomalies in the field by comparing the sensor data, for every attribute.

LIST OF RELATED ART DOCUMENTS

Patent Documents

Patent Document 1: European Patent Laid-Open Publication No. 3046066
Patent Document 2: Japanese Patent Laid-Open Publication No. 2012-164109

SUMMARY OF INVENTION

Problems to be Solved by the Invention

According to the system disclosed in the abovementioned Patent Documents 1 and 2, support for producers becomes possible, based on sensor data, but a large number of sensors need to be installed for that purpose. In particular, irrigation equipment that is installed in a field is laid over a wide area and is further provided with a large number of jet nozzles, and thus a huge number of sensors will be needed in order to reliably detect anomalies.

An exemplary object of the invention is to provide a field management apparatus, a field management method and a computer readable recording medium that solve the abovementioned problems, and that enable anomalies of equipment in a field to be detected without increasing the number of sensors.

Means for Solving The Problems

In order to achieve the above object, a field management apparatus in one aspect of the invention includes:
a learning model generation unit configured to generate a learning model, by using an image of a phenomenon that results from a fault in field equipment and an image of a phenomenon that results from normal operation of the field equipment to learn a feature amount of the image of the phenomenon that results from the fault in the field equipment;
an image acquisition unit configured to acquire an aerial image of a target region;
an image specification unit configured to apply the aerial image acquired by the image acquisition unit to the learning model generated by the learning model generation unit, and specify an image of the phenomenon that results from the fault in the field equipment in the aerial image acquired by the image acquisition unit: and
a fault location specification unit configured to specify a fault location of the field equipment in the target region, based on the image of the phenomenon that results from the fault in the field equipment specified by the image specification unit.

Also, in order to achieve the above object, a field management method in one aspect of the invention includes:
(a) a step of generating a learning model, by using an image of a phenomenon that results from a fault in field equipment and an image of a phenomenon that results from normal operation of the field equipment to learn a feature amount of the image of the phenomenon that results from the fault in the field equipment;
(b) a step of acquiring an aerial image of a target region;
(c) a step of applying the aerial image acquired in the (b) step to the learning model generated in the (a) step, and specifying an image of the phenomenon that results from the fault in the field equipment in the aerial image acquired in the (b) step; and
(d) a step of specifying a fault location of the field equipment in the target region, based on the image of the phenomenon that results from the fault in the field equipment specified in the (c) step.

Furthermore, in order to achieve the above object, a computer readable recording medium in one aspect of the invention includes a program recorded thereon, the program including instructions that cause a computer to carry out:
(a) a step of generating a learning model, by using an image of a phenomenon that results from a fault in field equipment and an image of a phenomenon that results from normal operation of the field equipment to learn a feature amount of the image of the phenomenon that results from the fault in the field equipment;

(b) a step of acquiring an aerial image of a target region;

(c) a step of applying the aerial image acquired in the (b) step to the learning model generated in the (a) step, and specifying an image of the phenomenon that results from the fault in the field equipment in the aerial image acquired in the (b) step; and (d) a step of specifying a fault location of the field equipment in the target region, based on the image of the phenomenon that results from the fault in the field equipment specified in the (c) step.

Advantageous Effects of the Invention

As described above, according to the invention, anomalies of equipment in a field can be detected, without increasing the number of sensors.

BRIEF DESCRIPTION OF THE DRAWINGS

FIG. 15 shows an example of partitions that are set in a target region in the fourth example embodiment of the invention.

EXAMPLE EMBODIMENTS

First Example Embodiment

Hereinafter, a field management apparatus, a field management method and a program in the first example embodiment of the invention will be described, with reference to FIGS. 1 to 6.

[Apparatus Configuration]

Figure 1:
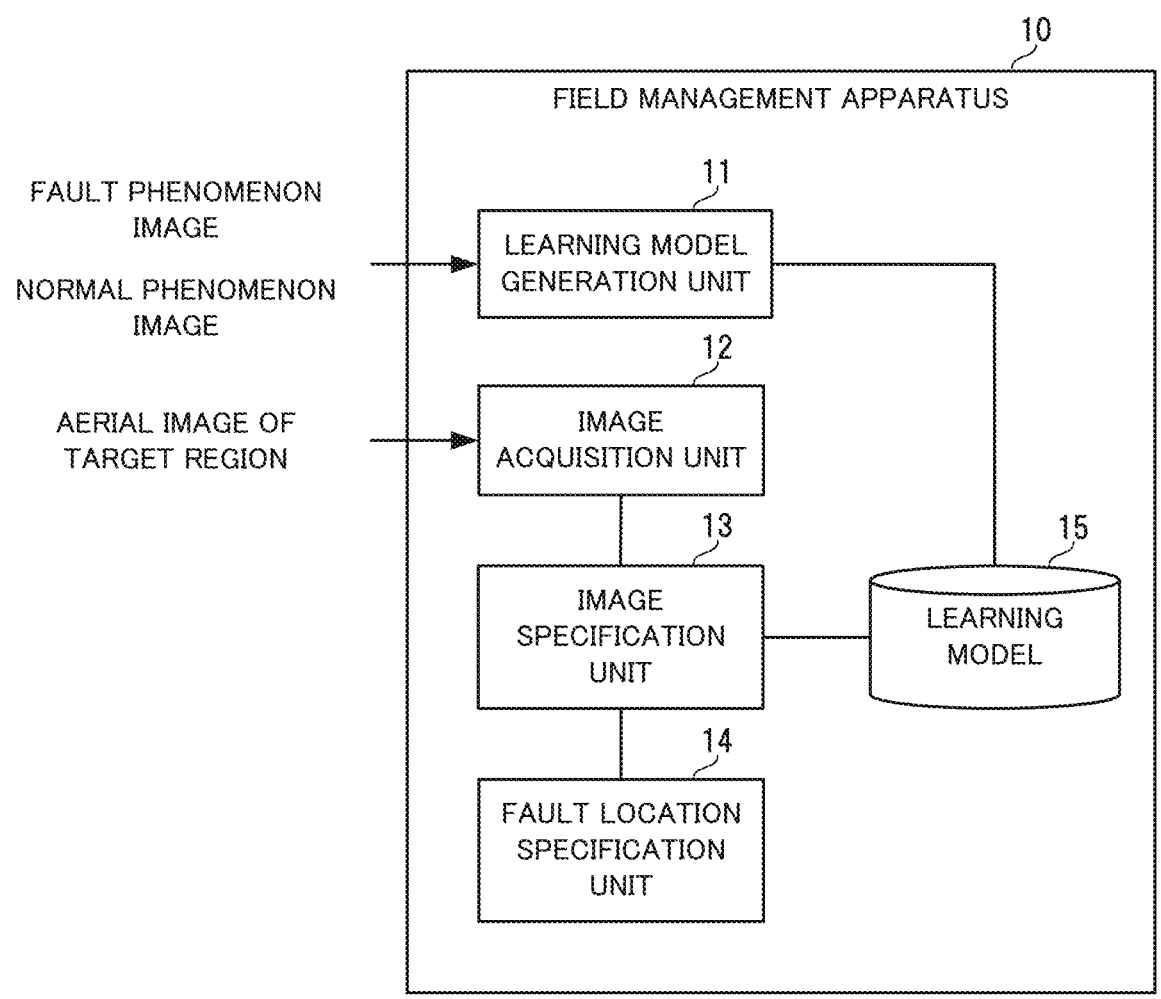
FIG. 1 is a block diagram showing the configuration of a field management apparatus in a first example embodiment of the invention.

Initially, a configuration of the field management apparatus in this first example embodiment will be described using FIG. 1. FIG. 1 is a block diagram showing the configuration of the field management apparatus in the first example embodiment of the invention.

A field management apparatus 10 in this first example embodiment shown in FIG. 1 is an apparatus for specifying a fault location of field equipment that is installed in a field. As shown in FIG. 1, the field management apparatus 10 is provided with a learning model generation unit 11, an image acquisition unit 12, an image specification unit 13, and a fault location specification unit 14.

The learning model generation unit 11 generates a learning model 15, by using images of phenomena that result from a fault in the field equipment (hereinafter, "fault phenomenon images") and images of phenomena that result from normal operation of field equipment (hereinafter, "normal phenomenon images") to learn feature amounts of the fault phenomenon images.

Here, the fault phenomenon images and the normal phenomenon images can be, for example, aerial images taken from above of a field serving as a target region. As described later, since the image that is applied to the learning model 15 is an aerial image, the images that the learning model generation unit 11 uses in generating the learning model 15 are also preferably aerial images.

Aerial images taken of a field from above are obtained by shooting the field from above using a satellite, a plane, a drone or the like, for example. In the case of using aerial images obtained by shooting a field from above with a satellite, a plane, a drone or the like, at the time of generating the learning model 15, there are times when a fault phenomenon image and a normal phenomenon image are contained in one aerial image. In the case where a fault phenomenon image and a normal phenomenon image are contained in one aerial image, the fault phenomenon image and the normal phenomenon image can be respectively clipped from the aerial image, and used in generating the learning model 15.

Also, in this embodiment, learning may be performed using "fault phenomenon images" and "images containing both a fault phenomenon image and a normal phenomenon image". In this case, improvement in the accuracy of the learning model can be expected. For example, assuming that the field equipment is irrigation equipment, and the phenomenon (fault phenomenon) that results from a fault is pooling of water due to leakage, in this case, no change in the outer shape of the equipment will be evident in the images between the case where the fault phenomenon has occurred and the normal case. Therefore, it becomes possible to learn features of fault phenomenon images more accurately, by using "images containing both a fault phenomenon image and a normal phenomenon image".

Accordingly, there are instances where performing learning by acquiring a large number of "fault phenomenon images" and "images containing both a fault phenomenon image and a normal phenomenon image" enables a learning model that more closely approximates the actual case to be generated. Furthermore, since cases where the fault phenomenon occurs at a position away from the field equipment are also conceivable, there are also instances where a learning model that even more closely approximates the actual case can be generated, by performing learning using "fault phenomenon images", "images containing a fault phenomenon image and a normal phenomenon image" and "normal phenomenon images".

The image specification unit 13 applies an aerial image acquired by the image acquisition unit 12 to the learning model 15 generated by the learning model generation unit 11, and specifies an image of the phenomenon that results from a fault in the field equipment (fault phenomenon image) in the aerial image acquired by the image acquisition unit 12.

The fault location specification unit 14 specifies the fault location of the field equipment in the target region, based on the fault phenomenon image specified by the image specification unit 13. For example, the fault location specification unit 14 is able to specify the fault location of the field equipment, based on position information included in the fault phenomenon image.

In this way, in this first example embodiment, the learning model generation unit 11 generates a learning model 15 that is able to specify fault phenomenon images by learning the feature amounts of fault phenomenon images, thus enabling fault phenomenon images to be accurately specified from aerial images. Thus, according to this first example embodiment, anomalies of equipment in a field can be detected, without increasing the number of sensors.

Figure 2:
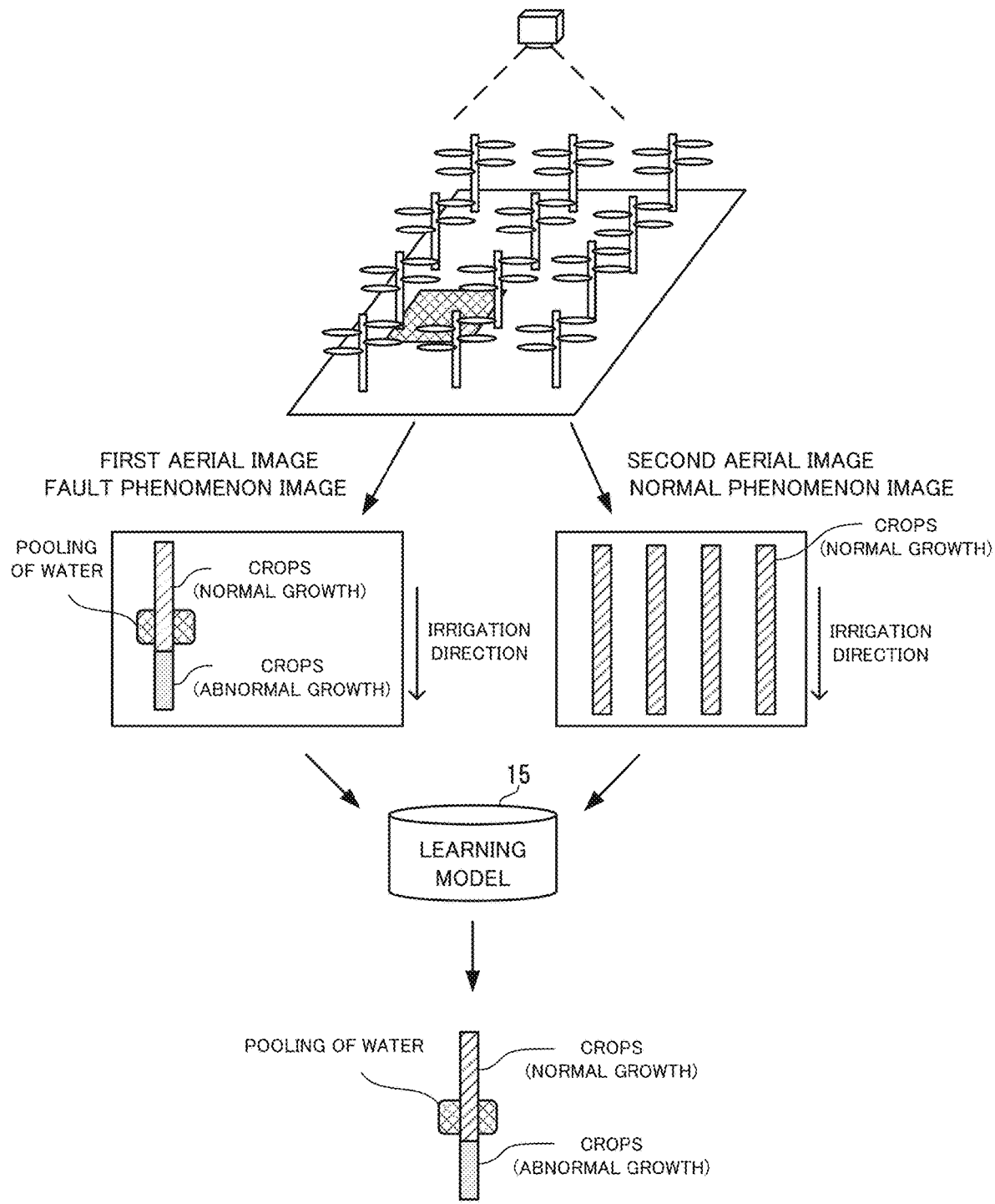
FIG. 2 illustrates processing for generating a learning model in the first example embodiment of the invention.
Figure 3:
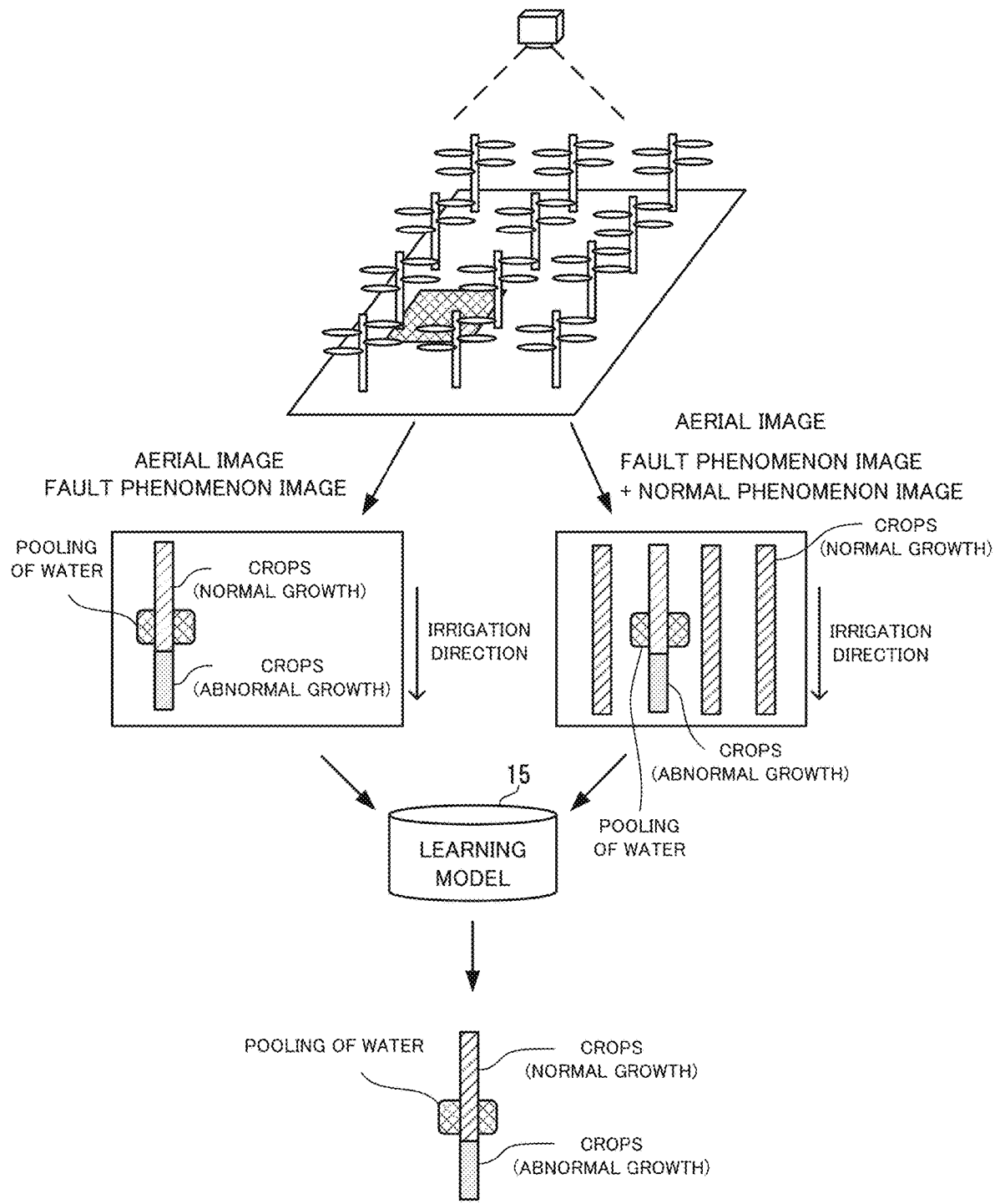
FIG. 3 illustrates another example of processing for generating a learning model in the first example embodiment of the invention.

Next, the configuration of the field management apparatus 10 in this first example embodiment will be more specifically described, using FIGS. 2 and 3. FIG. 2 illustrates processing for generating a learning model in the first example embodiment of the invention. In FIG. 2, an example using aerial images of a field or the like as the images that are used in generating a learning model is illustrated.

First, in this first example embodiment, "images" are assumed to all be visible images. Also, the field equipment that is targeted for fault location specification is assumed to be irrigation equipment. The irrigation equipment is, for example, provided with pipes disposed underground or above ground along furrows in a field. Also, holes are provided in the walls of the pipes at set intervals in the longitudinal direction of the pipes. In this irrigation equipment, when irrigation water is supplied to the pipes, the irrigation water is expelled to the field through the holes in the pipe walls, and supplied to crops.

Incidentally, with irrigation equipment having such a configuration, there are times when the pipes split due to degradation or when the pipes are cut. There are also times when the holes in the pipe walls get clogged, resulting in pressure building elsewhere and causing splits. In such cases, fault phenomena include phenomena that occur due to leakage of irrigation water, such as water pooling, furrows collapsing and changes in the growth of crops, for example.

Note that changes in the growth of crops refers to cases such as a slowdown in growth in areas that are not getting any water due to leakage, an acceleration in growth in areas where there is much moisture and a slowdown in growth in areas where there is not much moisture in the case where fertilizers are supplied by being dissolved in irrigation water, or withering of crops that are in areas where pools of water form, due to the roots not being able to respire.

Accordingly, in this first example embodiment, the learning model generation unit 11, using images of phenomena that occur due to leakage of irrigation water as fault phenomenon images, generates a learning model, by learning feature amounts of the images. This will now be described specifically as follows.

As shown in FIG. 2, first, images of a field are taken from above by a satellite, a plane, a drone or the like, and aerial images to be used in learning are obtained. Also, an aerial image containing a fault phenomenon image, among the obtained aerial images, is given as a first aerial image. On the other hand, an aerial image containing a normal phenomenon image is given as a second aerial image. Note that, in the case where an aerial image obtained by shooting contains both a fault phenomenon image and a normal phenomenon image, the first aerial image and the second aerial image may be created by processing the image. In the first aerial image shown in FIG. 2, water reaches to where there is pooling in the irrigation direction, and thus growth of the crops is considered to be normal. On the other hand, water does not reach beyond where there is pooling due to leakage, for example, and thus growth of the crops is slow and the leaves are pale green.

The learning model generation unit 11, in this first example embodiment, first acquires first and second aerial images obtained as described above. Note that although the number of first aerial images and second aerial images that are acquired is not limited, the largest possible number is desirable in terms of the discrimination accuracy of the learning model.

As described above, when leakage of irrigation water occurs, phenomena such as water pooling, furrows collapsing and changes in the growth of crops arise. Accordingly, the learning model generation unit 11 extracts, for example, the reflectance of light, the shape of the region where crops exist, the color of the region where crops exist and the periphery thereof and the position of the region where crops exist from the first aerial images, as feature amounts of images of phenomena that occur due to leakage of irrigation water.

Furthermore, the learning model generation unit 11 extracts the shape, color and position of the region where crops exist in a state where irrigation water is not leaking from the second aerial images, as feature amounts of normal phenomenon images. The learning model generation unit 11 then classifies and holds the feature amounts obtained from the first aerial images and the feature amounts obtained from the second aerial images.

Note that the shape of the region where crops exist includes shapes particular to targeted crops, the shape of furrows, and the like. Also, the shapes particular to crops refers to particular shapes when the crops are seen from above, which are determined by the leaf shape of the crops and how the leaves overlap. Furthermore, the position of the region where crops exist includes the state in which furrows are arrayed in the field. Also, the color of the region where crops exist includes frequency characteristics (color components including infrared and ultraviolet) in that region, which are determined by the crops and the leaf color thereof.

Next, the learning model generation unit 11 learns the feature amounts of the fault phenomenon images using a support vector machine. Specifically, the learning model generation unit 11 causes the support vector machine to learn the boundary between the fault phenomenon images and the normal phenomenon images by providing the feature amounts of the classified aerial images, and generates a learning model 15 indicating a learning result.

Also, the learning model generation unit 11 executes deep learning, using a large number of acquired first aerial images and second aerial images, and is thereby also able to create a classifier for identifying first aerial images and second aerial images, and set the created classifier as the learning model 15.

The image specification unit 13 specifies a fault phenomenon image from an aerial image acquired by the image acquisition unit 12, using the learning model 15 generated by the learning model generation unit 11. The aerial image that is acquired by the image acquisition unit 12 is also obtained by taking an image of a field or the like from above using a satellite, a plane, a drone or the like, similarly to the aerial images (refer to FIG. 2) that are used in learning.

The fault location specification unit 14, in the case where the image specification unit 13 is able to specify a fault phenomenon image from an aerial image, specifies the position of the fault phenomenon image in the field, and sets the specified position as the fault location. The fault location specification unit 14 is also able to notify the specified fault location to a terminal device of an administrator of the field management apparatus 10 or the like. The fault location can be displayed on the terminal device that has received notification of the fault location. Also, the terminal device that has received notification of the fault location is, for example, able to obtain highly accurate simulation results in various types of simulations such as growth simulation, by excluding the data collected at the fault location.

FIG. 3 illustrates another example of processing for generating a learning model in the first example embodiment of the invention. In the example in FIG. 3, the learning model generation unit 11 performs learning using "fault phenomenon images" and "images containing both a fault phenomenon image and a normal phenomenon image". As mentioned previously, the accuracy of the learning model improves as a result of performing learning using "fault phenomenon images" and "images containing both a fault phenomenon image and a normal phenomenon image".

[Apparatus Operations]

Next, operations of the field management apparatus 10 in the first example embodiment of the invention will be described using FIGS. 4 to 6. Also, in this first example embodiment, a field management method is implemented by operating the field management apparatus 10. Therefore, description of the field management method in this first example embodiment will be replaced by the following description of the operations of the field management apparatus 10.

Initially, processing for generating a learning model will be described using FIGS. 4 and 5. First, the case where a learning model is generated by a support vector machine will be described using FIG. 4. FIG. 4 is a flowchart showing operations at the time of learning model generation processing by the support vector machine of the field management apparatus in the first example embodiment of the invention.

Figure 4:
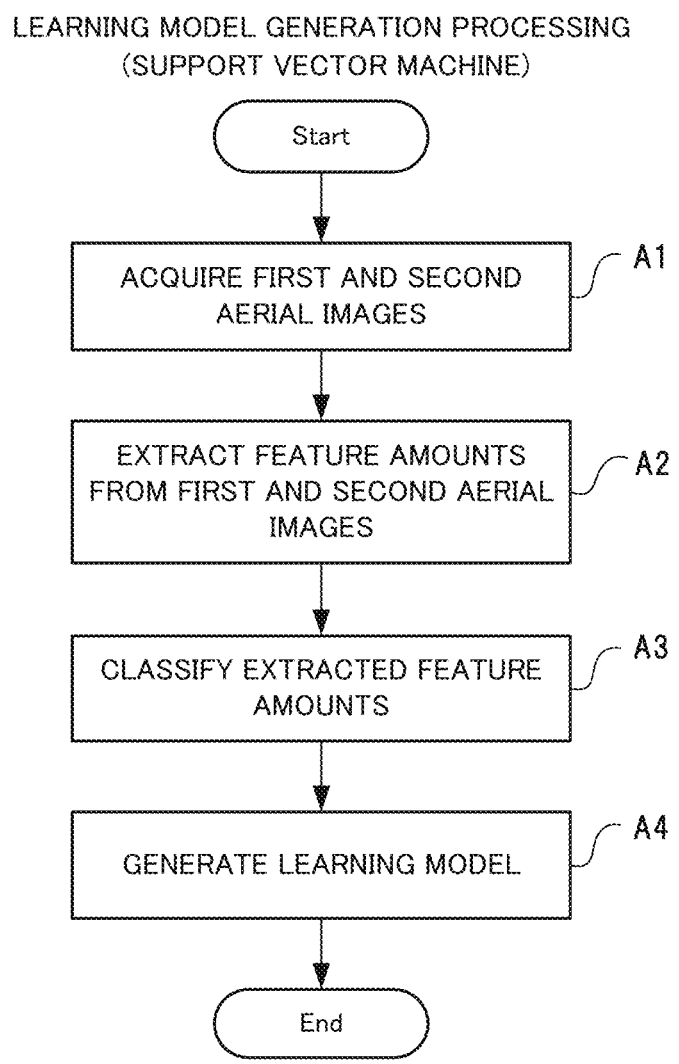
FIG. 4 is a flowchart showing operations at the time of learning model generation processing by a support vector machine of the field management apparatus in the first example embodiment of the invention.

As shown in FIG. 4, the learning model generation unit 11 acquires a large number of first aerial images and second aerial images from outside (step A1). The first aerial images and second aerial images are as described above.

Next, the learning model generation unit 11 extracts feature amounts of fault phenomenon images, that is, images of phenomena that occur due to leakage of irrigation water, from the first aerial images acquired in step A1, and extracts feature amounts of normal phenomenon images from the second aerial images (step A2).

Next, the learning model generation unit 11 classifies and holds the feature amounts obtained from the first aerial images and the feature amounts obtained from the second aerial images (step A3).

Next, the learning model generation unit 11 learns the feature amounts of the fault phenomenon images, that is, images of phenomena that occur due to leakage of irrigation water, using the support vector machine, and generates the learning model 15 (step A4).

Specifically, the learning model generation unit 11 causes the support vector machine to learn the boundary between the fault phenomenon images and the normal phenomenon images by providing the feature amounts of the classified aerial images, and generates a learning model 15 indicating a learning result.

Next, the case where a learning model is generated by deep learning will be described using FIG. 5. FIG. 5 is a flowchart showing operations at the time of learning model generation processing by deep learning of the field management apparatus in the first example embodiment of the invention.

Figure 5:
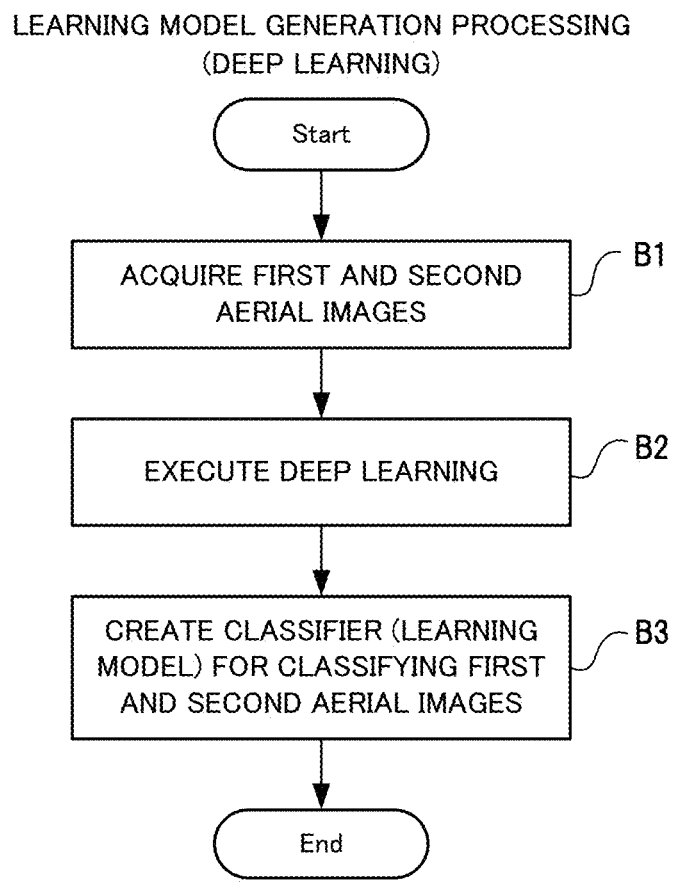
FIG. 5 is a flowchart showing operations at the time of learning model generation processing by deep learning of the field management apparatus in the first example embodiment of the invention.

As shown in FIG. 5, the learning model generation unit 11 acquires a large number of first aerial images and second aerial images from outside (step B1).

Next, the learning model generation unit 11 executes deep learning, using the large number of first aerial images and second aerial images acquired in step B1 (step B2).

The learning model generation unit 11 then creates a classifier for identifying first aerial images and second aerial images from the result of step B2, and sets the created classifier as the learning model 15 (step B3).

Next, processing for specifying a fault location will be described using FIG. 6. FIG. 6 is a flowchart showing operations at the time of fault location specification processing of the field management apparatus in the first example embodiment of the invention.

Figure 6:
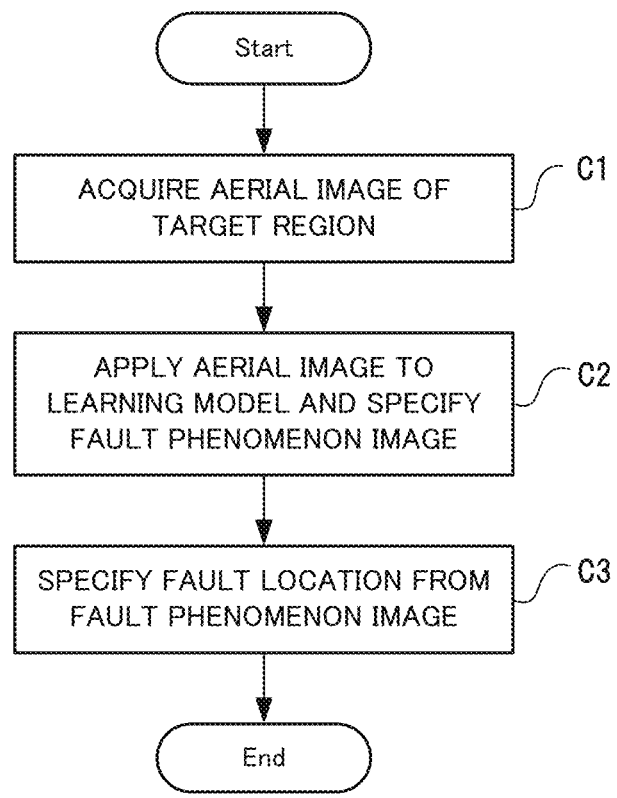
FIG. 6 is a flowchart showing operations at the time of fault location specification processing of the field management apparatus in the first example embodiment of the invention.

As shown in FIG. 6, initially, the image acquisition unit 12 acquires an aerial image of a field serving as the target region (step C1).

Next, the image specification unit 13 applies the aerial image acquired by the image acquisition unit 12 in step C1 to the learning model 15, and specifies a fault phenomenon image in this aerial image (step C2).

Next, the fault location specification unit 14 specifies the fault location of the irrigation equipment in the target region, using the fault phenomenon image specified by the image specification unit 13 in step C2 (step C3). Also, the fault location specification unit 14 notifies the specified fault location to an external terminal device or the like.

As described above, by executing steps A1 to A4 shown in FIG. 4 or steps B1 to B3 shown in FIG. 5, the learning model generation unit 11 learns the feature amounts of fault phenomenon images, and generates a learning model 15 that is able to specify fault phenomenon images. The image specification unit 13 is able to specify a fault phenomenon image, such as an image of pooled water, for example, by applying aerial images of the target region to this learning model 15. The fault location specification unit 14 then specifies the fault location of the irrigation equipment using the fault phenomenon image specified by the image specification unit 13. Thus, according to this first example embodiment, anomalies in field equipment can be detected, without increasing the number of sensors. In order to ascertain the situation of field equipment, dedicated sensors need to be installed for every item that is to be ascertained, and the cost of sensor installation and maintenance increases. In this first example embodiment, use of aerial images that are used by agricultural support services, for example, enables information relating to the situation of field equipment to be provided in conjunction with agricultural support services, without separately installing dedicated sensors.

[Program]

The program in this first example embodiment need only be a program that causes a computer to execute steps A1 to A4 shown in FIG. 4 (or steps B1 to B3 shown in FIG. 5) and steps C1 to C3 shown in FIG. 6. The field management apparatus 10 and the field management method in this first example embodiment can be realized, by this program being installed on a computer and executed. In this case, a processor of the computer functions and performs processing as the learning model generation unit 11, the image acquisition unit 12, the image specification unit 13, and the fault location specification unit 14.

Also, the program in this first example embodiment may be executed by a computer system built with a plurality of computers. In this case, for example, the computers may respectively function as one of the learning model generation unit 11, the image acquisition unit 12, the image specification unit 13, and the fault location specification unit 14.

Second Example Embodiment

Next, a field management apparatus, a field management method and a program in this second example embodiment will be described using FIGS. 7 to 11.

(Apparatus Configuration)

Initially, the configuration of the field management apparatus in the second example embodiment will be described. The field management apparatus in this second example embodiment has a similar configuration to the field management apparatus 10 shown in FIG. 1. Thus, in the following description, FIG. 1 will be referred to as appropriate. This second example embodiment, however, uses radar images as fault phenomenon images, normal phenomenon images and aerial images, and differs from the first example embodiment in this respect. Hereinafter, description will be given focusing on the differences from the first example embodiment.

First, the radar images that are used in this second example embodiment are images taken with a synthetic aperture radar mounted in a satellite, a plane or the like. Accordingly, in this embodiment the learning model generation unit 11 generates the learning model 15, by using radar images of phenomena that result from a fault in field equipment (hereinafter, "fault phenomenon radar images") and radar images of phenomena that result from normal operation of field equipment (hereinafter, "normal phenomenon radar images") to learn feature amounts of the fault phenomenon radar images.

Figure 7:
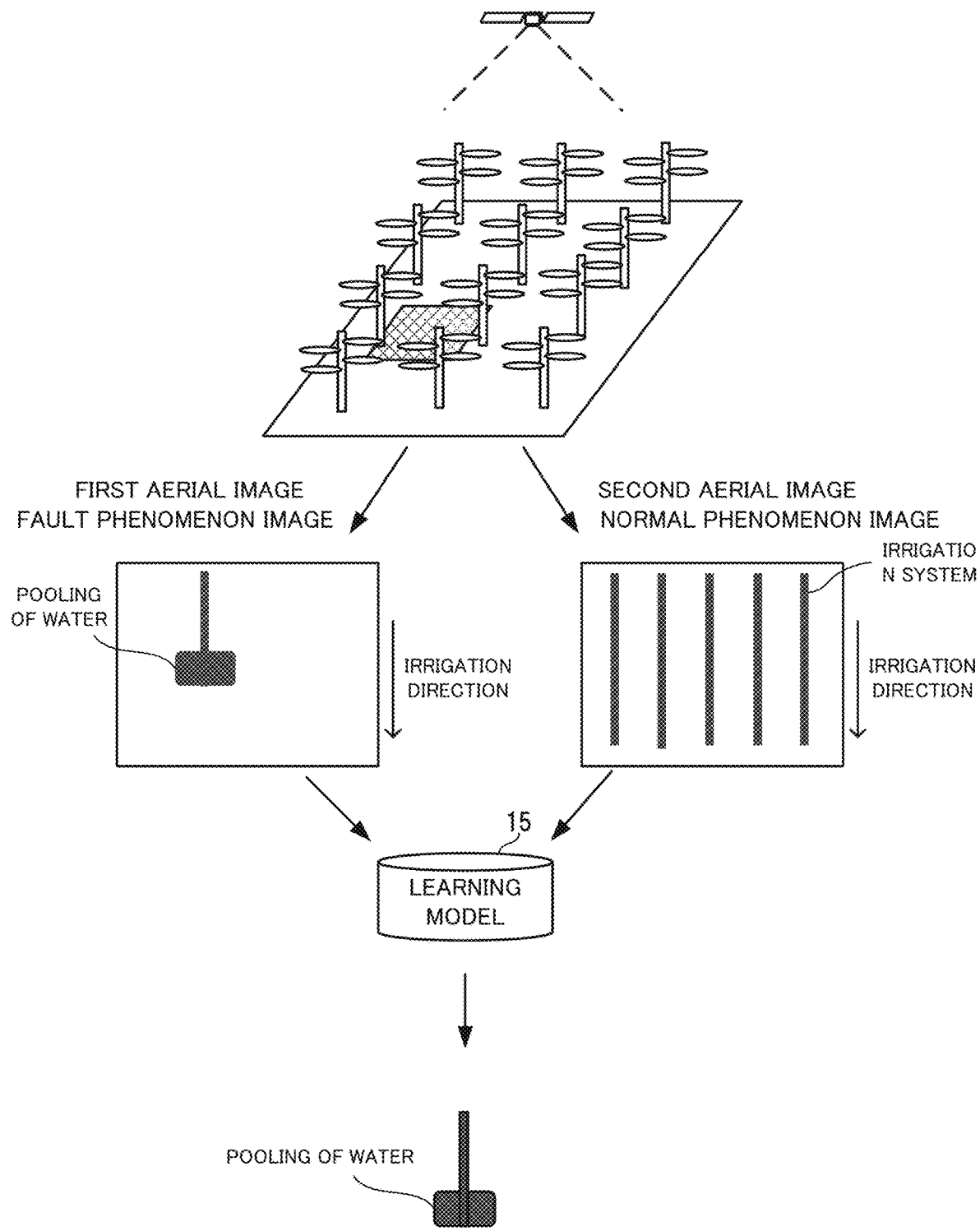
FIG. 7 illustrates processing for generating a learning model in a second example embodiment of the invention.

FIG. 7 illustrates processing for generating a learning model in the second example embodiment of the invention. As shown in FIG. 7, first, images of a field are taken from above with a synthetic aperture radar mounted in a satellite, a plane or the like, and radar images taken from above (hereinafter, "aerial radar images") to be used in learning are obtained. Also, an aerial radar image containing a fault phenomenon radar image, among the obtained aerial radar images, is given as a first aerial radar image. On the other hand, an aerial radar image containing a normal phenomenon radar image is given as a second aerial radar image. Note that, in the case where an aerial radar image obtained by shooting contains both a fault phenomenon radar image and a normal phenomenon radar image, the first aerial radar image and the second aerial radar image may be created by processing the image.

The learning model generation unit 11, in this second example embodiment, first acquires first and second aerial radar images obtained as described above. Note that although the number of first aerial radar images and second aerial radar images that are acquired is not limited, the largest possible number is desirable in terms of the discrimination accuracy of the learning model.

Incidentally, radar images are images formed based on the intensity of reflective waves from a radar that are irradiated from above. The intensity of the reflective waves changes depending on the state of the ground. Thus, radar images can be used as images that visualize the moisture content distribution of the ground surface.

As described in the first example embodiment, when leakage of irrigation water occurs, phenomena such as water pooling in the field arise, and the moisture content distribution on the ground surface or the ground near the surface changes. Accordingly, the learning model generation unit 11 extracts, for example, the moisture content gradient and the position and size of regions where the moisture content is estimated to be greater than or equal to a threshold (or less than or equal to a threshold) from the first aerial radar images, as feature amounts of radar images of phenomena that occur due to leakage of irrigation water.

Furthermore, the learning model generation unit 11 extracts, for example, the moisture content gradient and the position and size of regions where the moisture content is estimated to be greater than or equal to a threshold (or less than or equal to a threshold) in the case where irrigation water is not leaking from the second aerial radar images, as feature amounts of normal phenomenon radar images. The learning model generation unit 11 then classifies and holds the feature amounts obtained from the first aerial radar images and the feature amounts obtained from the second aerial radar images.

Note that, in the example of FIG. 7, the learning model generation unit 11 extracts the position and size of regions where the moisture content is estimated to be greater than or equal to a threshold, as feature amounts, from both the first aerial radar images and the second aerial radar images.

Next, the learning model generation unit 11 learns the feature amounts of the fault phenomenon radar images, using a support vector machine, similarly to the case of the first example embodiment. Specifically, the learning model generation unit 11 causes the support vector machine to learn the boundary between the fault phenomenon radar images and the normal phenomenon radar images by providing the feature amounts of the classified aerial radar images, and generates a learning model 15 indicating a learning result.

Also, the learning model generation unit 11 executes deep learning, using a large number of acquired first aerial radar images and second aerial radar images, and is thereby also able to create a classifier for identifying first aerial radar images and second aerial radar images, and set the created classifier as the learning model 15.

The image acquisition unit 12, in this second example embodiment, acquires a radar image taken from above (hereinafter, "aerial radar image") of the target region where a field exists. The image acquisition unit 12 acquires the aerial radar image of the field or the like taken from above with a synthetic aperture radar mounted in a satellite, a plane or the like, for example.

The image specification unit 13, in this second example embodiment, specifies a fault phenomenon radar image from the aerial radar image acquired by the image acquisition unit 12, using the learning model 15.

The fault location specification unit 14, in this second example embodiment, in the case where the image specification unit 13 is able to specify a fault phenomenon radar image from an aerial radar image, specifies the position of the fault phenomenon radar image in the field, and sets the specified position as the fault location. The fault location specification unit 14 is also able to notify the specified fault location to a terminal device of an administrator of the field management apparatus 10 or the like.

Figure 8:
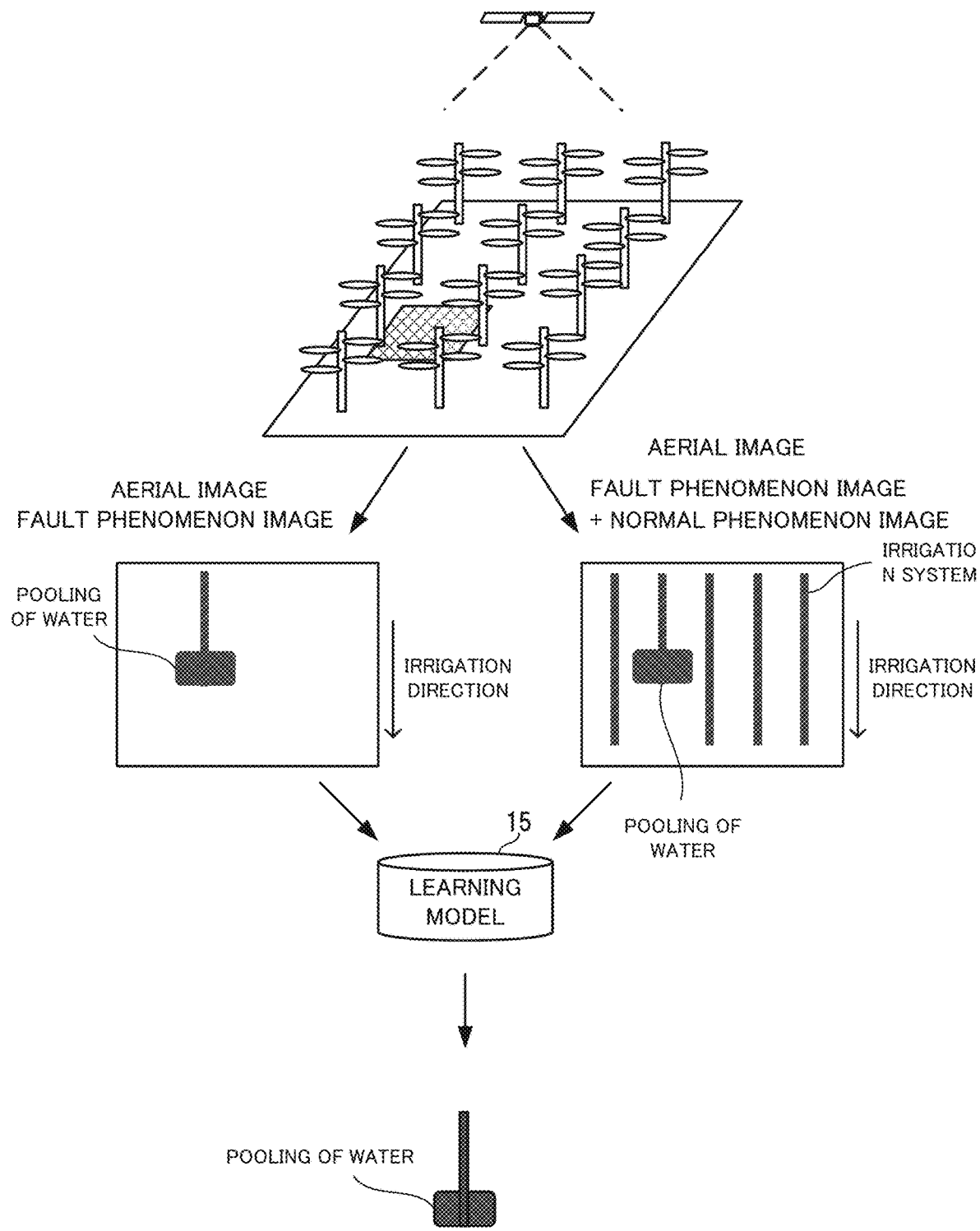
FIG. 8 illustrates another example of processing for generating a learning model in the second example embodiment of the invention.

FIG. 8 illustrates another example of processing for generating a learning model in the second example embodiment of the invention. In the example of FIG. 8, the learning model generation unit 11 performs learning using "fault phenomenon radar images" and "images containing both a fault phenomenon radar image and a normal phenomenon radar image". Improvement in the accuracy of the learning model can be expected as a result of performing learning using "fault phenomenon radar images" and "images containing both a fault phenomenon radar image and a normal phenomenon radar image".

[Apparatus Operations]

Next, operations of the field management apparatus in the second example embodiment of the invention will be described using FIGS. 9 to 11. Also, in this second example embodiment, a field management method is similarly implemented by operating the field management apparatus 10. Description of the field management method in this second example embodiment will be replaced by the following description of the operations of the field management apparatus 10.

Initially, processing for generating a learning model will be described using FIGS. 9 and 10. First, the case where a learning model is generated by a support vector machine will be described using FIG. 9. FIG. 9 is a flowchart showing operations at the time of learning model generation processing by the support vector machine of the field management apparatus in the second example embodiment of the invention.

Figure 9:
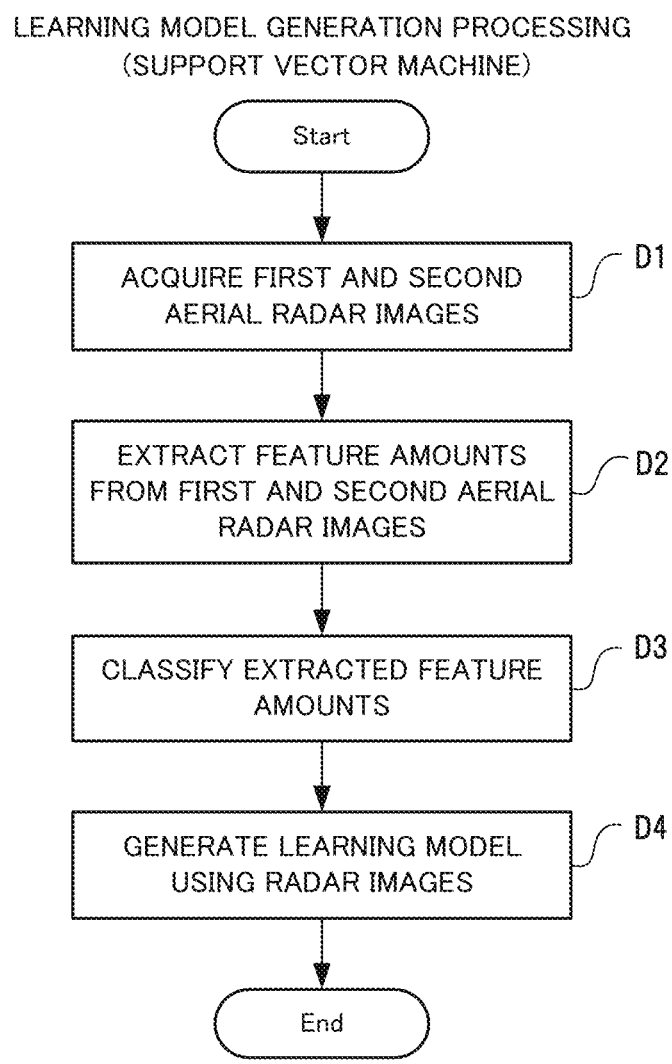
FIG. 9 is a flowchart showing operations at the time of learning model generation processing by a support vector machine of the field management apparatus in the second example embodiment of the invention.

As shown in FIG. 9, the learning model generation unit 11 acquires a large number of first aerial radar images and second aerial radar images from outside (step D1). The first aerial radar images and second aerial radar images are as described above.

Next, the learning model generation unit 11 extracts feature amounts of fault phenomenon radar images, that is, radar images of phenomena that occur due to leakage of irrigation water, from the first aerial radar images acquired in step D1, and extracts feature amounts of normal phenomenon radar images from the second aerial radar images (step D2).

Next, the learning model generation unit 11 classifies and holds the feature amounts obtained from the first aerial radar images and the feature amount obtained from the second aerial radar images (step D3).

Next, the learning model generation unit 11 learns the feature amounts of the fault phenomenon images, that is, radar images of phenomena that occur due to leakage of irrigation water, using the support vector machine, and generates the learning model 15 (step D4).

Specifically, the learning model generation unit 11 causes the support vector machine to learn the boundary between the fault phenomenon radar images and the normal phenomenon radar images by providing the feature amounts of the classified aerial radar images, and generates a learning model 15 indicating a learning result.

Next, the case where a learning model is generated by deep learning will be described using FIG. 10. FIG. 10 is a flowchart showing operations at the time of learning model generation processing by deep learning of the field management apparatus in the second example embodiment of the invention.

Figure 10:
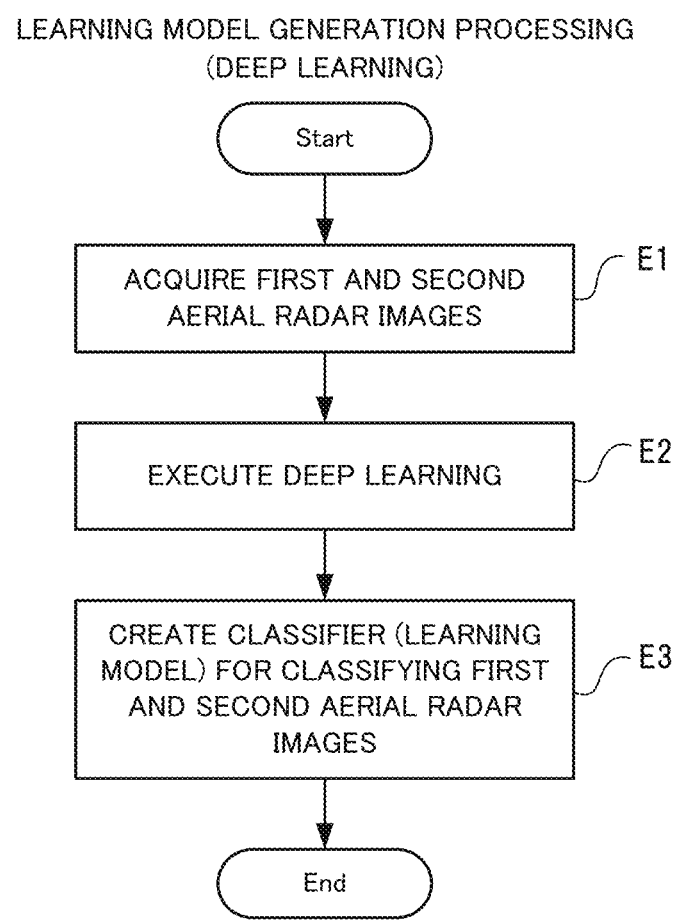
FIG. 10 is a flowchart showing operations at the time of learning model generation processing by deep learning of the field management apparatus in the second example embodiment of the invention.

As shown in FIG. 10, the learning model generation unit 11 acquires a large number of first aerial radar images and second aerial radar images from outside (step E1).

Next, the learning model generation unit 11 executes deep learning, using the large number of first aerial radar images and second aerial radar images acquired in step E1 (step E2).

The learning model generation unit 11 then creates a classifier for identifying first aerial radar images and second aerial radar images from the result of step E2, and sets the created classifier as the learning model 15 (step E3).

Next, fault location specification processing will be described using FIG. 11. FIG. 11 is a flowchart showing operations at the time of fault location specification processing of the field management apparatus in the second example embodiment of the invention.

Figure 11:
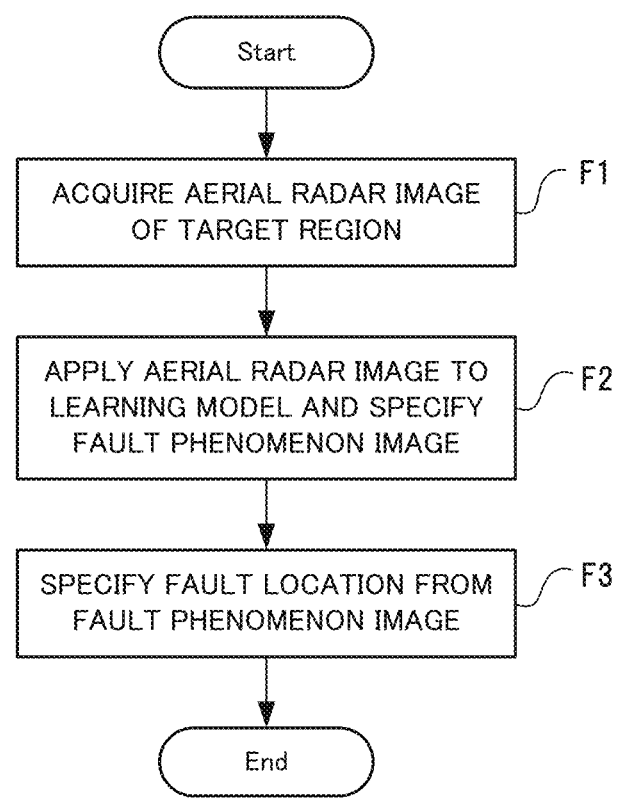
FIG. 11 is a flowchart showing operations at the time of fault location specification processing of the field management apparatus in the second example embodiment of the invention.

As shown in FIG. 11, initially, the image acquisition unit 12 acquires an aerial radar image of a field serving as the target region (step F1).

Next, the image specification unit 13 applies the aerial radar image acquired by the image acquisition unit 12 in step F1 to the learning model 15, and specifies a fault phenomenon radar image in this aerial radar image (step F2).

Next, the fault location specification unit 14 specifies the fault location of the irrigation equipment in the target region, using the fault phenomenon radar image specified by the image specification unit 13 in step F2 (step F3). Also, the fault location specification unit 14 notifies the specified fault location to an external terminal device or the like.

As described above, in this second example embodiment, the learning model generation unit 11 generates the learning model 15 from radar images. Thus, according to this second example embodiment, leakage that cannot be distinguished with a visible image can be specified, and thus early detection of fault locations can be expected.

[Program]

The program in this second example embodiment need similarly only be a program that causes a computer to execute steps D1 to D4 shown in FIG. 9 (or steps E1 to E3 shown in FIG. 10), and steps F1 to F3 shown in FIG. 11. The field management apparatus and the field management method in the second example embodiment can be realized, by this program being installed on a computer and executed. In this case, a CPU (Central Processing Unit) of the computer functions and performs processing as the learning model generation unit 11, the image acquisition unit 12, the image specification unit 13, and the fault location specification unit 14.

Also, the program in this second example embodiment may similarly be executed by a computer system built with a plurality of computers. In this case, for example, the computers may respectively function as one of the learning model generation unit 11, the image acquisition unit 12, the image specification unit 13, and the fault location specification unit 14.

Third Example Embodiment

Next, a field management apparatus, a field management method and a program in this third example embodiment will be described using FIGS. 12 and 13.

[Apparatus Configuration]

Initially, a configuration of the field management apparatus in this third example embodiment will be described using FIG. 12. FIG. 12 is a block diagram showing the configuration of the field management apparatus in the third example embodiment of the invention.

Figure 12:
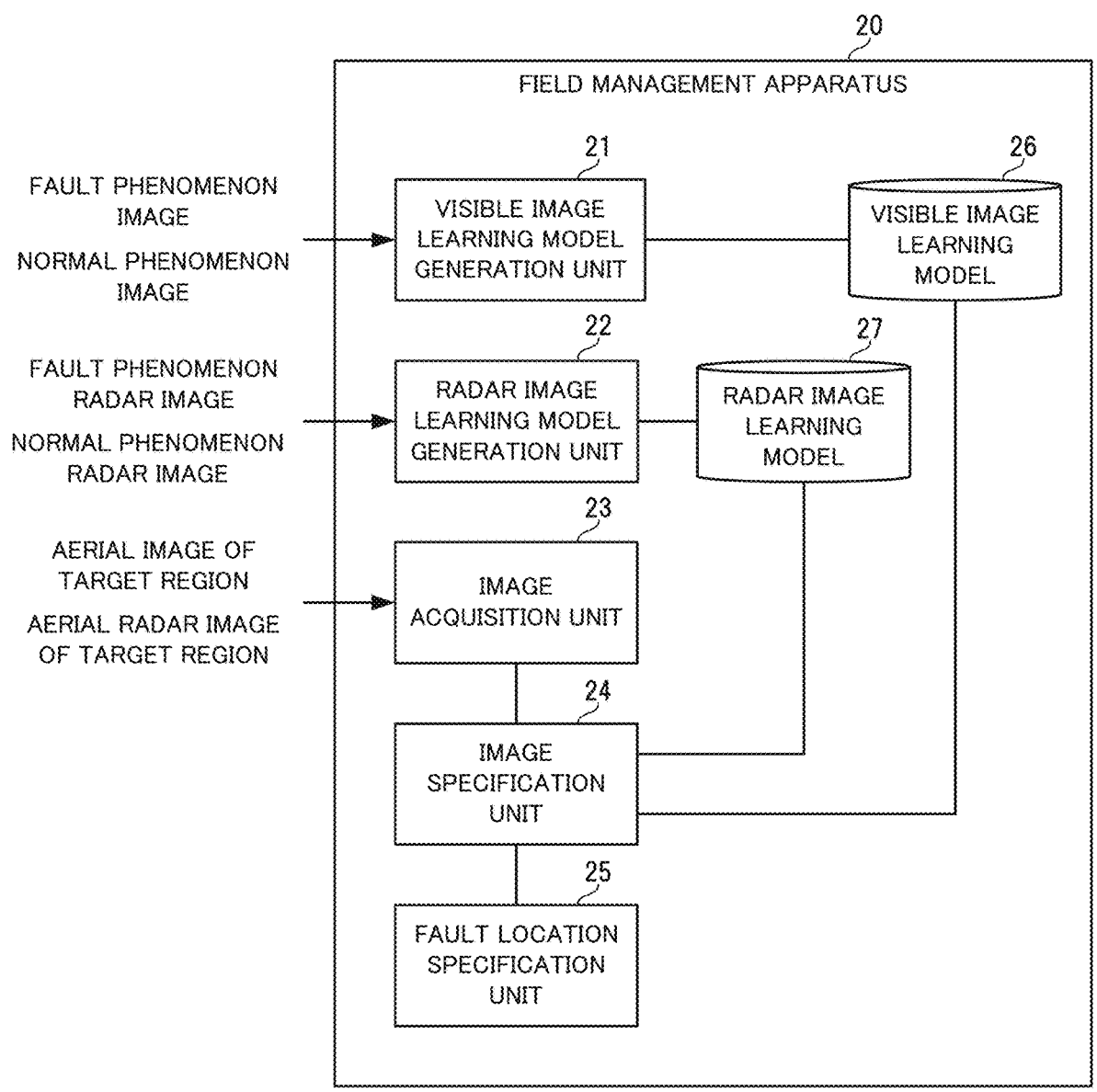
FIG. 12 is a block diagram showing the configuration of a field management apparatus in a third example embodiment of the invention.

As shown in FIG. 12, the field management apparatus 20 in this third example embodiment is provided with a visible image learning model generation unit 21, a radar image learning model generation unit 22, an image acquisition unit 23, an image specification unit 24, and a fault location specification unit 25.

The field management apparatus 20 in this third example embodiment differs from the field management apparatus 10 in the first example embodiment shown in FIG. 1 in terms of being provided with two learning model generation units, namely, the visible image learning model generation unit 21 and the radar image learning model generation unit 22. Also, the respective processing of the image acquisition unit 23, the image specification unit 24 and the fault location specification unit 25 also thereby differs from the first example embodiment. Hereinafter, description will be given focusing on the differences from the first and second example embodiments.

First, the visible image learning model generation unit 21 is similar to the learning model generation unit 11 in the first example embodiment shown in FIG. 1. The visible image learning model generation unit 21 generates a visual image learning model 26 by using a fault phenomenon image and a normal phenomenon image to learn feature amounts of the fault phenomenon image. Note that the fault phenomenon images and the normal phenomenon images are visible images. Also, the visual image learning model 26 is created by the learning processing described in the first example embodiment, and is built similarly to the learning model 15 shown in the first example embodiment.

Also, the radar image learning model generation unit 22 is similar to the learning model generation unit in the second example embodiment. The radar image learning model generation unit 22 generates a radar image learning model 27, by using a fault phenomenon radar image and a normal phenomenon radar image to learn feature amounts of the fault phenomenon radar image. Note that the radar image learning model 27 is created by the learning processing described in the second example embodiment, and is built similarly to the learning model shown in the second example embodiment.

The image acquisition unit 23, in this third example embodiment, acquires a visible image of the target region taken from above, and a radar image of the target region taken from above. In other words, in this third example embodiment, the image acquisition unit 23 acquires two types of images, namely, the image acquired in the first example embodiment and the image acquired in the second example embodiment.

The image specification unit 24, first, applies the visible image of the target region taken from above acquired by the image acquisition unit 23 to the visual image learning model 26 generated by the visible image learning model generation unit 21, and specifies a fault phenomenon image (visible image) in the visible image of the target region taken from above. Also, the image specification unit 24 applies the radar image taken from above acquired by the image acquisition unit 23 to the radar image learning model 27 generated by the radar image learning model generation unit 22, and specifies a fault phenomenon radar image in the radar image of the target region taken from above.

Also, the fault location specification unit 25 specifies the fault location of the field equipment in the target region, based on the fault phenomenon image specified by the image specification unit 24, and the fault phenomenon radar image similarly specified by the image specification unit 24. Specifically, the fault location specification unit 25 compares the fault location specified by the visible image with the fault location specified by the radar image. The fault location specification unit 25, in the case where the visual image and the radar image coincide, then takes the location specified by both these images as the fault location. On the other hand, the fault location specification unit 25, in the case where the visual image and the radar image do not coincide, takes a location specified by one of these images as the fault location, according to the situation. For example, in the case where pipes for irrigation equipment are buried underground, and water tends not to precipitate to the surface of the field, the fault location specification unit 25 gives preference to the fault location specified by the radar image.

[Apparatus Operations]

Next, operations of the field management apparatus 20 in the third example embodiment of the invention will be described using FIG. 13. Also, in this third example embodiment, a field management method is implemented by operating the field management apparatus 20. Therefore, description of the field management method in this third example embodiment will be replaced by the following description of the operations of the field management apparatus 20.

First, in this third example embodiment, the visible image learning model generation unit 21 executes processing according to steps A1 to A4 shown in FIG. 4 or steps B1 to B3 shown in FIG. 5, and generates the visual image learning model 26. Also, the radar image learning model generation unit 22 executes processing according to steps D1 to D4 shown in FIG. 9 or steps E1 to E3 shown in FIG. 10, and generates the radar image learning model 27.

Next, fault location specification processing will be described using FIG. 13. FIG. 13 is a flowchart showing operations at the time of fault location specification processing of the field management apparatus in the third example embodiment of the invention.

Figure 13:
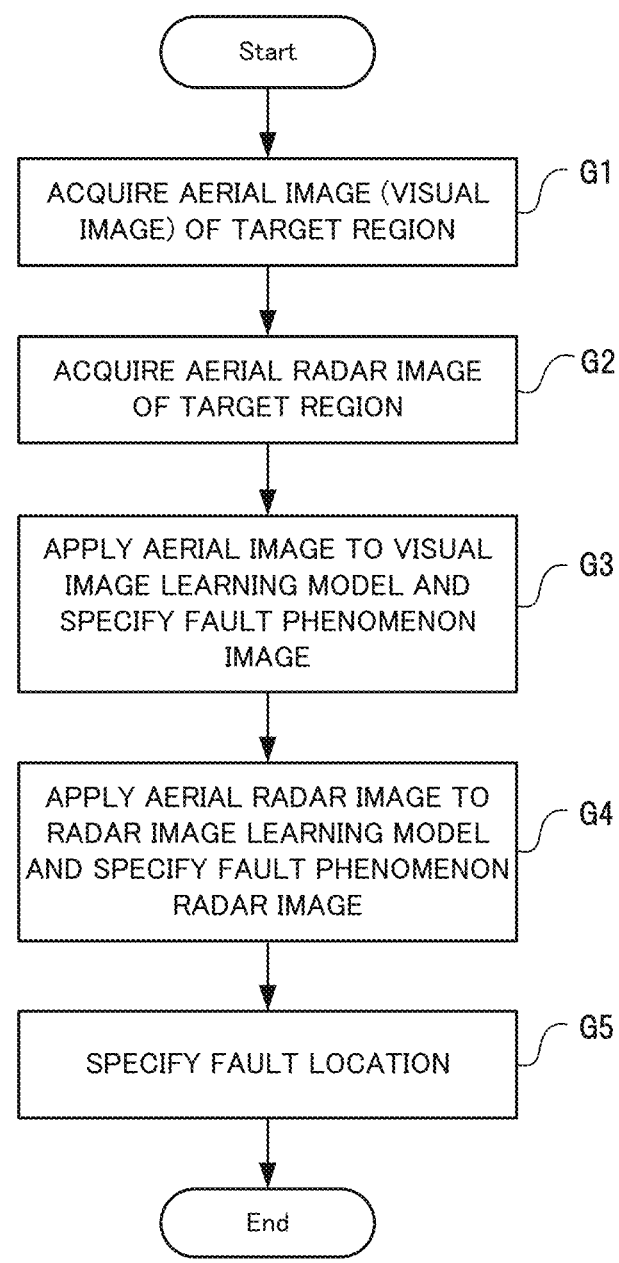
FIG. 13 is a flowchart showing operations at the time of fault location specification processing of the field management apparatus in the third example embodiment of the invention.

As shown in FIG. 13, initially, the image acquisition unit 23 acquires an aerial image (visible image) of a field serving as the target region (step G1). Next, the image acquisition unit 23 acquires an aerial radar image of the field serving as the target region (step G2).

Next, the image specification unit 24 applies the aerial image acquired by the image acquisition unit 23 in step G1 to the visual image learning model 26, and specifies a fault phenomenon image in this aerial image (step G3). Next, the image specification unit 24 applies the aerial radar image acquired by the image acquisition unit 23 in step G2 to the radar image learning model 27, and specifies a fault phenomenon radar image in this aerial radar image (step G4).

Next, the fault location specification unit 25 specifies the fault location of the field equipment in the target region, based on the fault phenomenon image specified by the image specification unit 24 in step G3 and the fault phenomenon radar image specified by the image specification unit 24 in step G4 (step G5). Also, the fault location specification unit 25 notifies the specified fault location to an external terminal device or the like.

As described above, in this third example embodiment, a learning model that uses the visible image described in the first example embodiment and a learning model that uses the radar image described in the second example embodiment are built, and the fault location is specified using both learning models, and it thus becomes possible to specify the fault location even more accurately.

[Program]

The program in this third example embodiment need only be a program that causes a computer to execute steps A1 to A4 shown in FIG. 4 (or steps B1 to B3 shown in FIG. 5), steps D1 to D4 shown in FIG. 9 (or steps E1 to E3 shown in FIG. 10), and steps G1 to G5 shown in FIG. 13. The field management apparatus 20 and the field management method in this third example embodiment can be realized, by this program being installed on a computer and executed. In this case, a processor of the computer functions and performs processing as the visible image learning model generation unit 21, the radar image learning model generation unit 22, the image acquisition unit 23, the image specification unit 24, and the fault location specification unit 25.

Also, the program in this third example embodiment may be executed by a computer system built with a plurality of computers. In this case, for example, the computers may respectively function as one of the visible image learning model generation unit 21, the radar image learning model generation unit 22, the image acquisition unit 23, the image specification unit 24, and the fault location specification unit 25.

Fourth Example Embodiment

Hereinafter, a field management apparatus, a field management method and a program in the fourth example embodiment of the invention will be described, with reference to FIGS. 14 to 16.

[Apparatus Configuration]

Initially, a configuration of the field management apparatus in this fourth example embodiment will be described using FIG. 14. FIG. 14 is a block diagram showing the configuration of the field management apparatus in the fourth example embodiment of the invention.

Figure 14:
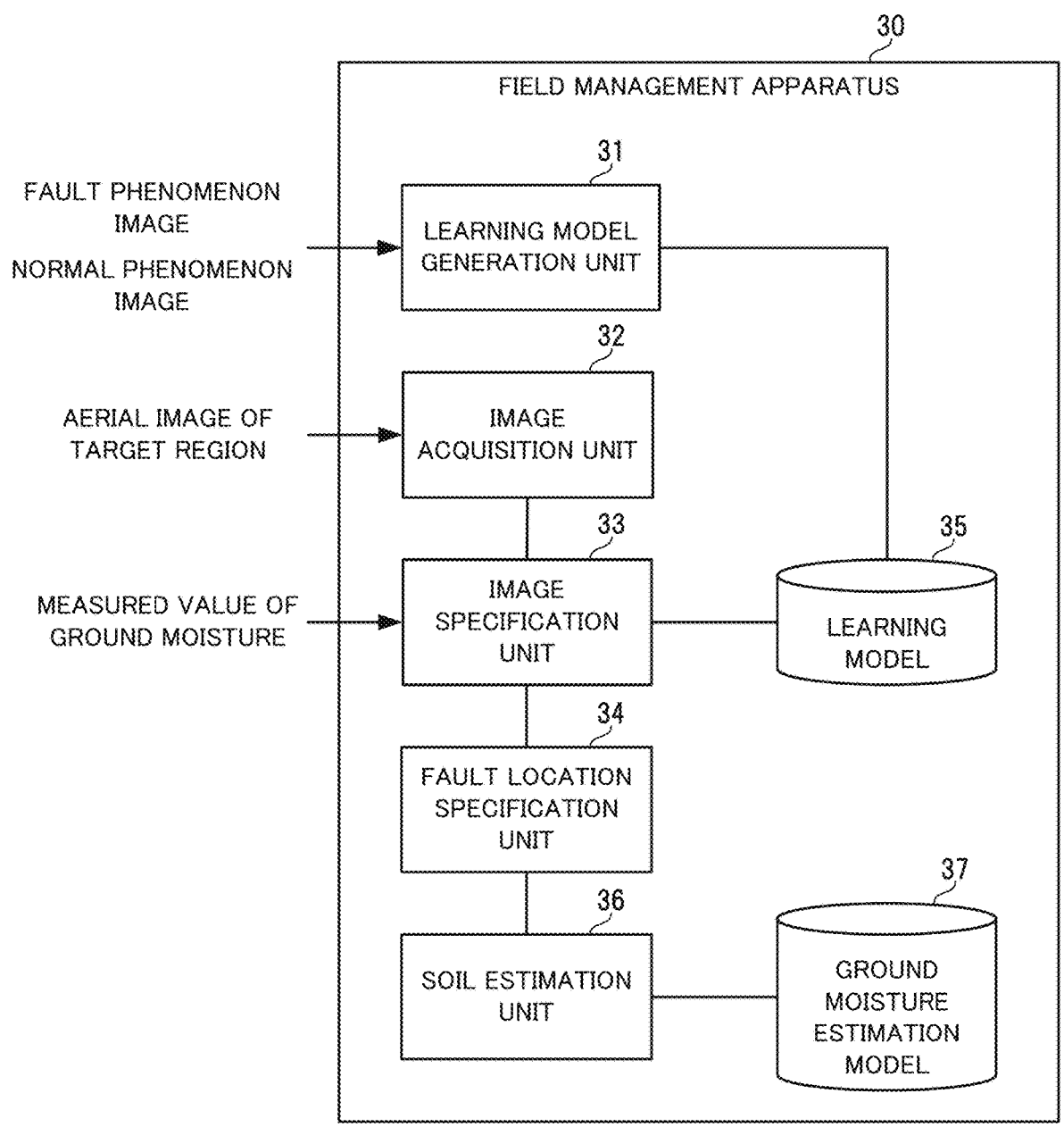
FIG. 14 is a block diagram showing the configuration of a field management apparatus in a fourth example embodiment of the invention.

As shown in FIG. 14, the field management apparatus 30 in this fourth example embodiment is provided with a learning model generation unit 31, an image acquisition unit 32, an image specification unit 33, a fault location specification unit 34, and a soil estimation unit 36.

The field management apparatus 30 in this fourth example embodiment differs from the field management apparatus 10 in the first example embodiment shown in FIG. 1 in terms of being provided with the soil estimation unit 36. Also, the processing in the fault location specification unit 34 also thereby differs from the first example embodiment. Hereinafter, description will be given focusing on the differences from the first example embodiment.

First, in this fourth example embodiment, the soil estimation unit 36 estimates the ground moisture amount of the target region. Specifically, the soil estimation unit 36, first, divides the target region of the field into a plurality of portions, and sets a plurality of partitions.

Figure 15:
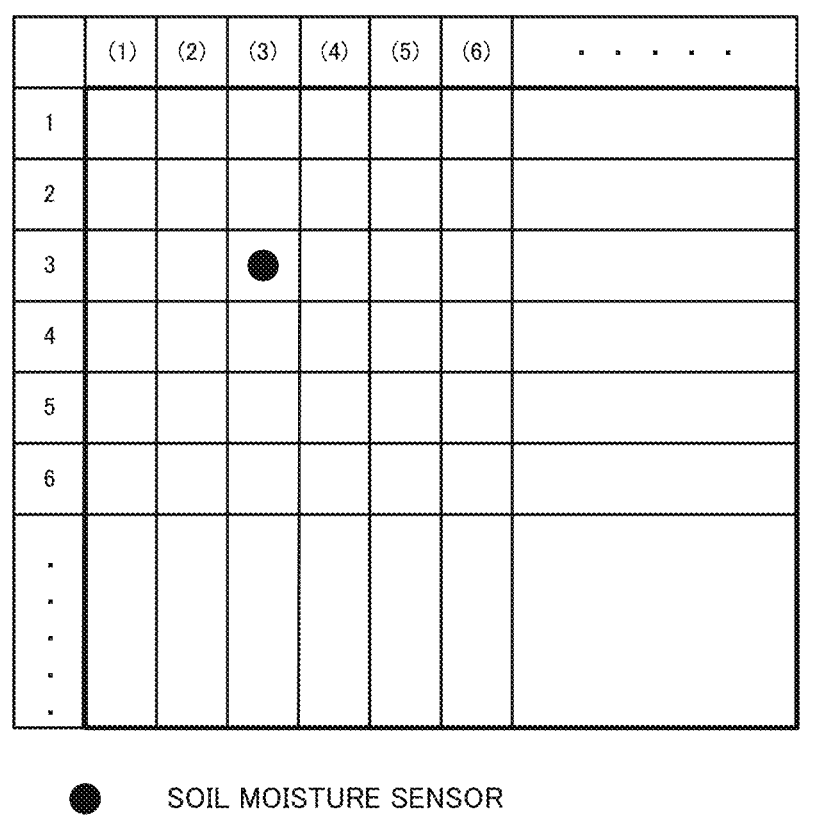

FIG. 15 shows an example of partitions set in a target region in the fourth example embodiment of the invention. In the example of FIG. 15, the soil estimation unit 36 has set the partitions, by dividing the target region into a grid. The accuracy of the estimation model improves as the area of each partition becomes smaller, that is, as the target field is partitioned into a finer mesh pattern.

Next, the soil estimation unit 36 predicts the inflow amount and outflow ground moisture amount, for every partition, based on both topographical information and soil distribution information, and generates a ground moisture estimation model 37. Specifically, the soil estimation unit 36, first, extracts corresponding topographical information and soil distribution information, for every partition, specifies the composition and slope of soil in each partition, and generates the ground moisture estimation model 37, based on the specified composition and slope of the soil.

The ground moisture estimation model 37 is a model that, from a measured value indicating the state of ground moisture at one point within the target region, and estimates the underground state at a different point from that one point. Topographical information is a topographical model representing the slope of a target field or the like, for example. Soil distribution information is a soil distribution model representing soil distribution in the target field, for example.

Next, the soil estimation unit 36 acquires a measured value from a soil moisture sensor that is installed in an arbitrary position of the target region, and estimates the amount of ground moisture, for every partition, by applying the measured value that is acquired to the ground moisture estimation model 37. In other words, the soil estimation unit 36 calculates the absolute value of the moisture amount in each partition, from the relative relationship of the moisture amounts in each partition, by inputting the measured value to the ground moisture estimation model 37. The distribution of the moisture amount in the target region can thereby be specified. That is, the moisture amount resulting from natural phenomena such as heavy rain can be specified using the ground moisture estimation model 37.

Also, in this fourth example embodiment, the fault location specification unit 34 specifies the fault location of the field equipment (irrigation equipment) in the target region, based on the fault phenomenon image specified by the image specification unit 33 and the ground moisture amount of the target region estimated by the soil estimation unit 36.

For example, the fault location specification unit 34 specifies the distributions of moisture amount of the location (location A) specified by the fault phenomenon image and the periphery thereof, and collates the specified distributions of moisture amount with the distributions of moisture amount of the location A and the periphery thereof specified by the soil estimation unit 36 using the ground moisture estimation model 37. Alternatively, the fault location specification unit 34 collates an image of the location A and the periphery thereof with the distribution of moisture amount of the location A and the periphery thereof specified by the soil estimation unit 36 using the ground moisture estimation model 37. For example, in the case where the distributions of moisture amount coincide, the fault phenomenon image is considered to be an image representing a phenomenon that results from a natural phenomenon, rather than an image representing a phenomenon that results from a fault in the irrigation equipment. In the case where the distributions of the moisture amount do not coincide, the fault phenomenon image is considered to be an image representing a phenomenon that results from a fault in the irrigation equipment. The fault location specification unit 34 takes the location specified by the fault phenomenon image as the fault location. It is thereby possible to prevent a phenomenon that results from a natural phenomenon being given as a phenomenon that results from a fault in the irrigation equipment.

[Apparatus Operations]

Next, operations of the field management apparatus 30 in the fourth example embodiment of the invention will be described using FIG. 16. Also, in this fourth example embodiment, a field management method is implemented by operating the field management apparatus 30. Therefore, description of the field management method in this fourth example embodiment will be replaced by the following description of the operations of the field management apparatus 30.

First, in this fourth example embodiment, the learning model generation unit 31 executes processing according to steps A1 to A4 shown in FIG. 4 or steps B1 to B3 shown in FIG. 5, similarly to the first example embodiment, and generates a learning model 35.

Next, fault location specification processing will be described using FIG. 16. FIG. 16 is a flowchart showing operations at the time of fault location specification processing of the field management apparatus in the fourth example embodiment of the invention.

Figure 16:
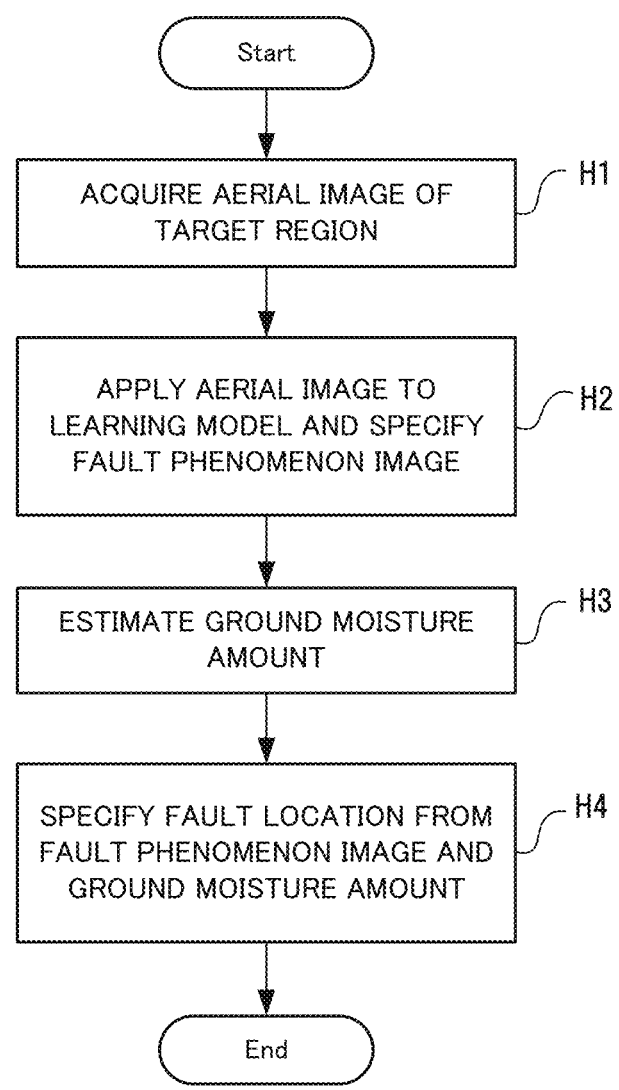
FIG. 16 is a flowchart showing operations at the time of fault location specification processing of the field management apparatus in the fourth example embodiment of the invention.

As shown in FIG. 16, initially, the image acquisition unit 32 acquires an aerial image of a field serving as the target region (step H1).

Next, the image specification unit 33 applies the aerial image acquired by the image acquisition unit 32 in step H1 to the learning model 35, and specifies a fault phenomenon image in this aerial image (step H2).

Next, the soil estimation unit 36 applies a measured value acquired from the soil moisture sensor to the ground moisture estimation model 37, and estimates the ground moisture amount, for every partition (step H3).

Next, the fault location specification unit 34 specifies the fault location of the field equipment in the target region, based on the fault phenomenon image specified by the image specification unit 33 in step H2 and the ground moisture amount for every partition of the target region estimated by the soil estimation unit 36 (step H4). Also, the fault location specification unit 34 notifies the specified fault location to an external terminal device or the like.

In this way, according to this fourth example embodiment, the ground moisture amount is calculated, and, by utilizing the result thereof, it can be confirmed whether the fault location specified from an aerial image really is a fault in the irrigation equipment. According to this fourth example embodiment, improvement in the specification accuracy of a fault location is achieved. Also, the soil estimation unit 36 that is used in this fourth example embodiment may be provided in the field management apparatus shown in the second and third example embodiments. Similar effects to the above can also be obtained in this case.

[Program]

The program in this fourth example embodiment need only be a program that causes a computer to execute steps A1 to A4 shown in FIG. 4 (or steps B1 to B3 shown in FIG. 5), and steps H1 to H4 shown in FIG. 16. The field management apparatus 30 and the field management method in this fourth example embodiment can be realized, by this program being installed on a computer and executed. In this case, a processor of the computer functions and performs processing as the learning model generation unit 31, the image acquisition unit 32, the image specification unit 33, the fault location specification unit 34, and the soil estimation unit 36.

Also, the program in this fourth example embodiment may be executed by a computer system built with a plurality of computers. In this case, for example, the computers may respectively function as one of the learning model generation unit 31, the image acquisition unit 32, the image specification unit 33, the fault location specification unit 34, and the soil estimation unit 36.

(Physical Configuration)

Figure 17:
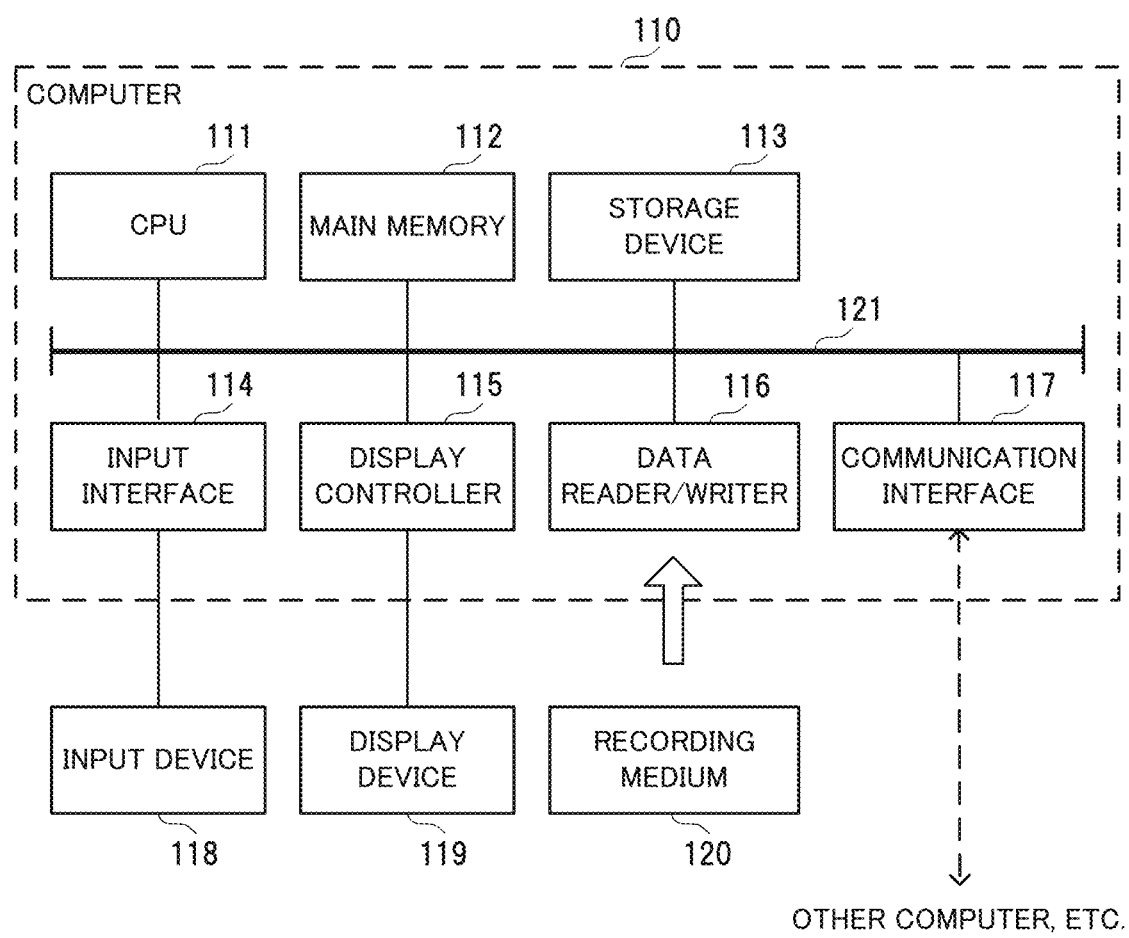
FIG. 17 is a block diagram showing an example of a computer that realizes a field management apparatus in the first to fourth example embodiments of the invention.

Here, a computer that realizes a field management apparatus by executing a program of the first to fourth example embodiments will be described using FIG. 17. FIG. 17 is a block diagram showing an example of a computer that realizes a field management apparatus in the first to fourth example embodiments of the invention.

As shown in FIG. 17, a computer 110 is provided with a CPU (Central Processing Unit) 111, a main memory 112, a storage device 113, an input interface 114, a display controller 115, a data reader/writer 116, and a communication interface 117. These units are connected to each other in a manner that enables data communication, via a bus 121.

The CPU 111 implements various computations, by extracting programs (code) of the example embodiments stored in the storage device 113 to the main memory 112, and executing these programs in predetermined order. The main memory 112 is, typically, a volatile storage device such as a DRAM (Dynamic Random Access Memory). Also, the programs of the example embodiments can be provided in a state of being stored on a computer readable recording medium 120. Note that the programs of the example embodiments may also be distributed on the Internet connected via the communication interface 117. Note that the computer 110 may be provided with a GPU (Graphics Processing Unit) or a FPGA (Field-Programmable Gate Array), in addition to the CPU 111 or instead of the CPU 111.

Also, a semiconductor memory device such as a flash memory is given as a specific example of the storage device 113, in addition to a hard disk drive. The input interface 114 mediates data transmission between the CPU 111 and an input device 118 such a keyboard and a mouse. The display controller 115 is connected to a display device 119, and controls display that is performed on the display device 119.

The data reader/writer 116 mediates data transmission between the CPU 111 and the recording medium 120, and executes reading out of programs from the recording medium 120, and writing of processing results of the computer 110 to the recording medium 120. The communication interface 117 mediates data transmission between the CPU 111 and other computers.

Also, a general-purpose semiconductor memory such as CF (Compact Flash (registered trademark)) and SD (Secure Digital), a magnetic recording medium such a flexible disk, or an optical recording medium such as CD-ROM (Compact Disk Read Only Memory) are given as specific examples of the recording medium 120.

Note that the field management apparatus in the example embodiments is also realizable by using hardware that supports the various components, rather than a computer on which programs are installed. Furthermore, the field management apparatus 10 may be partly realized by programs, and the remaining portion may be realized by hardware.

The above example embodiments can also be partly or wholly represented by (Supplementary Note 1) to (Supplementary Note 24) described below, but are not limited to the following disclosure.

(Supplementary Note 1)

A field management apparatus including:

a learning model generation unit configured to generate a learning model, by using an image of a phenomenon that results from a fault in field equipment and an image of a phenomenon that results from normal operation of the field equipment to learn a feature amount of the image of the phenomenon that results from the fault in the field equipment;

an image acquisition unit configured to acquire an aerial image of a target region;

an image specification unit configured to apply the aerial image acquired by the image acquisition unit to the learning model generated by the learning model generation unit, and specify an image of the phenomenon that results from the fault in the field equipment in the aerial image acquired by the image acquisition unit; and a fault location specification unit configured to specify a fault location of the field equipment in the target region, based on the image of the phenomenon that results from the fault in the field equipment specified by the image specification unit.

(Supplementary Note 2)

The field management apparatus according to supplementary note 1, in which the learning model generation unit:

extracts the feature amount of the phenomenon that results from the fault in the field equipment from the image of the phenomenon that results from the fault in the field equipment, extracts a feature amount of the phenomenon that results from normal operation of the field equipment from the image of the phenomenon that results from normal operation of the field equipment, and learns the feature amount of the image of the phenomenon that results from the fault in the field equipment using a support vector machine, and generates a learning model indicating a learning result.

(Supplementary Note 3)

The field management apparatus according to supplementary note 1, in which the learning model generation unit creates, by deep learning, a classifier for identifying the image of the phenomenon that results from the fault in the field equipment and the image of the phenomenon that results from normal operation of the field equipment, and sets the created classifier as the learning model.

(Supplementary Note 4)

The field management apparatus according to any of supplementary notes 1 to 3, in which the image of the phenomenon that results from the fault in the field equipment, the image of the phenomenon that results from normal operation of the field equipment and the aerial image are visible images.

(Supplementary Note 5)

The field management apparatus according to any of supplementary notes 1 to 3, in which the image of the phenomenon that results from the fault in the field equipment, the image of the phenomenon that results from normal operation of the field equipment and the aerial image are radar images.

(Supplementary Note 6)

The field management apparatus according to supplementary note 4, further including:

a second learning model generation unit configured to generate a second learning model, by using a radar image of the phenomenon that results from the fault in the field equipment and a radar image of the phenomenon that results from normal operation of the field equipment to learn a feature amount of the radar image of the phenomenon that results from the fault in the field equipment, in which the image acquisition unit acquires a visible image of the target region taken from above and a radar image of the target region taken from above, the image specification unit:

applies the visible image of the target region taken from above acquired by the image acquisition unit to the learning model generated by the learning model generation unit, and specifies a visible image of the phenomenon that results from the fault in the field equipment in the visible image of the target region taken from above acquired by the image acquisition unit, and applies the radar image of the target region taken from above acquired by the image acquisition unit to the second learning model generated by the second learning model generation unit, and specifies a radar image of the phenomenon that results from the fault in the field equipment in the radar image of the target region taken from above acquired by the image acquisition unit, and the fault location specification unit specifies the fault location of the field equipment in the target region, based on the visible image of the phenomenon that results from the fault in the field equipment and the radar image of the phenomenon that results from the fault in the field equipment specified by the image specification unit.

(Supplementary Note 7)

The field management apparatus according to any of supplementary notes 1 to 6, in which the field equipment is irrigation equipment, and the phenomenon that results from the fault in the field equipment is a phenomenon that occurs due to leakage of irrigation water.

(Supplementary Note 8)

The field management apparatus according to supplementary note 7, further including:

a soil estimation unit configured to estimate a ground moisture amount of the target region, in which the fault location specification unit specifies the fault location of the field equipment in the target region, based on the image of the phenomenon that results from the fault in the field equipment specified by the image specification unit and the ground moisture amount of the target region estimated by the soil estimation unit.

(Supplementary Note 9)

A field management method including:

(a) a step of generating a learning model, by using an image of a phenomenon that results from a fault in field equipment and an image of a phenomenon that results from normal operation of the field equipment to learn a feature amount of the image of the phenomenon that results from the fault in the field equipment;

(b) a step of acquiring an aerial image of a target region;

(c) a step of applying the aerial image acquired in the (b) step to the learning model generated in the (a) step, and specifying an image of the phenomenon that results from the fault in the field equipment in the aerial image acquired in the (b) step; and (d) a step of specifying a fault location of the field equipment in the target region, based on the image of the phenomenon that results from the fault in the field equipment specified in the (c) step.

(Supplementary Note 10)

The field management method according to supplementary note 9, in which, in the (a) step:

the feature amount of the phenomenon that results from the fault in the field equipment is extracted from the image of the phenomenon that results from the fault in the field equipment, a feature amount of the phenomenon that results from normal operation of the field equipment is extracted from the image of the phenomenon that results from normal operation of the field equipment, and the feature amount of the image of the phenomenon that results from the fault in the field equipment is learned using a support vector machine, and a learning model indicating a learning result is generated.

(Supplementary Note 11)

The field management method according to supplementary note 9, in which, in the (a) step, a classifier for identifying the image of the phenomenon that results from the fault in the field equipment and the image of the phenomenon that results from normal operation of the field equipment is created by deep learning, and the created classifier is set as the learning model.

(Supplementary Note 12)

The field management method apparatus according to any of supplementary notes 9 to 11, in which the image of the phenomenon that results from the fault in the field equipment, the image of the phenomenon that results from normal operation of the field equipment and the aerial image are visible images.

(Supplementary Note 13)

The field management method apparatus according to any of supplementary notes 9 to 11, in which the image of the phenomenon that results from the fault in the field equipment, the image of the phenomenon that results from normal operation of the field equipment and the aerial image are radar images.

(Supplementary Note 14)

The field management method according to supplementary note 12, further including:

(e) a step of generating a second learning model, by using a radar image of the phenomenon that results from the fault in the field equipment and a radar image of the phenomenon that results from normal operation of the field equipment to learn a feature amount of the radar image of the phenomenon that results from the fault in the field equipment, in which, in the (b) step, a visible image of the target region taken from above and a radar image of the target region taken from above are acquired, in the (c) step:

the visible image of the target region taken from above acquired in the (b) step is applied to the learning model generated in the (a) step, and a visible image of the phenomenon that results from the fault in the field equipment is specified in the visible image of the target region taken from above acquired in the (b) step, and the radar image of the target region taken from above acquired in the (b) step is applied to the second learning model generated in the (e) step, and a radar image of the phenomenon that results from the fault in the field equipment is specified in the radar image of the target region taken from above acquired in the (b) step, and in the (d) step, the fault location of the field equipment in the target region is specified, based on the visible image of the phenomenon that results from the fault in the field equipment and the radar image of the phenomenon that results from the fault in the field equipment specified in the (c) step.

(Supplementary Note 15)

The field management method according to any of supplementary notes 9 to 14, in which the field equipment is irrigation equipment, and the phenomenon that results from the fault in the field equipment is a phenomenon that occurs due to leakage of irrigation water.

(Supplementary Note 16)

The field management method according to supplementary note 15, further including:

(f) a step of estimating a ground moisture amount of the target region, in which, in the (d) step, the fault location of the field equipment in the target region is specified, based on the image of the phenomenon that results from the fault in the field equipment specified in the (c) step and the ground moisture amount of the target region estimated in the (f) step.

(Supplementary Note 17)

A computer readable recording medium that includes a program recorded thereon, the program including instructions that cause a computer to carry out:

(a) a step of generating a learning model, by using an image of a phenomenon that results from a fault in field equipment and an image of a phenomenon that results from normal operation of the field equipment to learn a feature amount of the image of the phenomenon that results from the fault in the field equipment;

(b) a step of acquiring an aerial image of a target region;

(c) a step of applying the aerial image acquired in the (b) step to the learning model generated in the (a) step, and specifying an image of the phenomenon that results from the fault in the field equipment in the aerial image acquired in the (b) step; and (d) a step of specifying a fault location of the field equipment in the target region, based on the image of the phenomenon that results from the fault in the field equipment specified in the (c) step.

(Supplementary Note 18)

The computer readable recording medium according to the supplementary note 17, in which, in the (a) step:

the feature amount of the phenomenon that results from the fault in the field equipment is extracted from the image of the phenomenon that results from the fault in the field equipment, a feature amount of the phenomenon that results from normal operation of the field equipment is extracted from the image of the phenomenon that results from normal operation of the field equipment, and the feature amount of the image of the phenomenon that results from the fault in the field equipment is learned using a support vector machine, and a learning model indicating a learning result is generated.

(Supplementary Note 19)

The computer readable recording medium according to the supplementary note 17, in which, in the (a) step, a classifier for identifying the image of the phenomenon that results from the fault in the field equipment and the image of the phenomenon that results from normal operation of the field equipment is created by deep learning, and the created classifier is set as the learning model.

(Supplementary Note 20)

The computer readable recording medium according to any of the supplementary notes 17 to 19, in which the image of the phenomenon that results from the fault in the field equipment, the image of the phenomenon that results from normal operation of the field equipment and the aerial image are visible images.

(Supplementary Note 21)

The computer readable recording medium according to any of the supplementary notes 17 to 19, in which the image of the phenomenon that results from the fault in the field equipment, the image of the phenomenon that results from normal operation of the field equipment and the aerial image are radar images.

(Supplementary Note 22)

The computer readable recording medium according to the supplementary note 20, the program including an instruction that causes a computer to carry out:

(e) a step of generating a second learning model, by using a radar image of the phenomenon that results from the fault in the field equipment and a radar image of the phenomenon that results from normal operation of the field equipment to learn a feature amount of the radar image of the phenomenon that results from the fault in the field equipment, in which, in the (b) step, a visible image of the target region taken from above and a radar image of the target region taken from above are acquired, in the (c) step:

the visible image of the target region taken from above acquired in the (b) step is applied to the learning model generated in the (a) step, and a visible image of the phenomenon that results from the fault in the field equipment is specified in the visible image of the target region taken from above acquired in the (b) step, and the radar image of the target region taken from above acquired in the (b) step is applied to the second learning model generated in the (e) step, and a radar image of the phenomenon that results from the fault in the field equipment is specified in the radar image of the target region taken from above acquired in the (b) step, and in the (d) step, the fault location of the field equipment in the target region is specified, based on the visible image of the phenomenon that results from the fault in the field equipment and the radar image of the phenomenon that results from the fault in the field equipment specified in the (c) step.

(Supplementary Note 23)

The computer readable recording medium according to any of the supplementary notes 17 to 22, in which the field equipment is irrigation equipment, and the phenomenon that results from the fault in the field equipment is a phenomenon that occurs due to leakage of irrigation water.

(Supplementary Note 24)

The computer readable recording medium according to the supplementary note 23, the program including an instruction that causes a computer to carry out:

(f) a step of estimating a ground moisture amount of the target region, in which, in the (d) step, the fault location of the field equipment in the target region is specified, based on the image of the phenomenon that results from the fault in the field equipment specified in the (c) step and the ground moisture amount of the target region estimated in the (f) step.

Although the invention has been described above with reference to example embodiments, the invention is not intended to be limited to the above example embodiments. A person skilled in the art will appreciate that the configurations and details of the invention can be variously modified within the scope of the invention.

This application is based upon and claims the benefit of priority from Japanese application No. 2017-66190 filed in Japan on Mar. 29, 2017, the disclosure of which is incorporated herein in its entirely.

INDUSTRIAL APPLICABILITY

As described above, according to the present invention, anomalies in field equipment can be detected, without increasing the number of sensors. The invention is useful in the agricultural field.

LIST OF REFERENCE SIGNS

10 Field management apparatus (first and second example embodiments)
11 Learning model generation unit
12 Image acquisition unit
13 Image specification unit
14 Fault location specification unit
15 Learning model
20 Field management apparatus (third example embodiment)
21 Visual image learning model generation unit
22 Radar image learning model generation unit
23 Image acquisition unit
24 Image specification unit
25 Fault location specification unit
26 Visible image learning model
27 Radar image learning model
30 Field management apparatus (fourth example embodiment)
31 Learning model generation unit
32 Image acquisition unit
33 Image specification unit
34 Fault location specification unit
35 Learning model
36 Soil estimation unit
37 Ground moisture estimation model
110 Computer
111 CPU
112 Main memory
113 Storage device
114 Input interface
115 Display controller
116 Data reader/writer
117 Communication interface
118 Input device
119 Display device
120 Recording medium
121 Bus

The invention claimed is:

1. A field management apparatus comprising:
at least one memory configured to store instructions
at least one processor coupled to the at least one memory and configured to execute the instructions to:
generate a learning model for determining whether an aerial image of a phenomenon results from a fault in a field equipment by using first feature amounts extracted from a first aerial image of the phenomenon that results from the fault in field equipment and second feature amounts extracted from a second aerial image of the phenomenon that results from normal operation of the field equipment, wherein the field equipment is irrigation equipment;

acquire a third aerial image of a target region;

apply the third aerial image of the target region to the learning model and specify the aerial image of the phenomenon that results from the fault in the field equipment; and specify a fault location of the field equipment in the target region, based on the aerial image of the phenomenon that results from the fault in the field equipment, wherein the first aerial image includes images showing one or more of water pooling, furrows collapsing in the field and changes in the growth of crops in the field caused by cracks and cuts in pipes installed in the field equipment or the field equipment failure, and the second aerial image does not include the first aerial image of the phenomenon that results from the fault in the field equipment.

2. The field management apparatus according to claim 1, wherein the at least one processor is further configured to execute the instructions to:

generate, by deep learning, a classifier for identifying the aerial image of the phenomenon that results from the fault in the field equipment and the aerial image of the phenomenon that results from normal operation of the field equipment, and set the created classifier as the learning model.

3. The field management apparatus according to claim 1, wherein the aerial image of the phenomenon that results from the fault in the field equipment, the aerial image of the phenomenon that results from normal operation of the field equipment and the aerial image are visible images.

4. The field management apparatus according to claim 1, wherein the aerial image of the phenomenon that results from the fault in the field equipment, the aerial image of the phenomenon that results from normal operation of the field equipment and the third aerial image are radar images.

5. The field management apparatus according to claim 3, further comprising:

wherein the at least one processor is further configured to execute the instructions to:

generate a second learning model, by using a radar image of the phenomenon that results from the fault in the field equipment and a radar image of the phenomenon that results from normal operation of the field equipment to learn a feature amount of the radar image of the phenomenon that results from the fault in the field equipment, acquire a visible image of the target region taken from above and a radar image of the target region taken from above, apply the visible image of the target region to the learning model and specify a visible image of the phenomenon that results from the fault in the field equipment in the visible image of the target region, and apply the radar image of the target region to the second learning model, and specify a radar image of the phenomenon that results from the fault in the field equipment in the radar image of the target region, and specify the fault location of the field equipment in the target region, based on the visible image of the phenomenon that results from the fault in the field equipment and the radar image of the phenomenon that results from the fault in the field equipment.

6. The field management apparatus according to claim 1, further comprising wherein the at least one processor is further configured to execute the instructions to:

estimate a ground moisture amount of the target region, and specify the fault location of the field equipment in the target region, based on the aerial image of the phenomenon that results from the fault in the field equipment and the ground moisture amount of the target region.

7. A field management method comprising:

(a) generating a learning model for determining whether an aerial image of a phenomenon results from a fault in a field equipment by using first feature amounts extracted from a first aerial image of the phenomenon that results from the fault in field equipment and second feature amounts extracted from a second aerial image of the phenomenon that results from normal operation of the field equipment, wherein the field equipment is irrigation equipment;

(b) acquiring a third aerial image of a target region;

(c) applying the third aerial image to the learning model and specifying the aerial image of the phenomenon that results from the fault in the field equipment; and (d) specifying a fault location of the field equipment in the target region, based on the aerial image of the phenomenon that results from the fault in the field equipment, wherein the first aerial image includes images showing one or more of water pooling, furrows collapsing in the field and changes in the growth of crops in the field caused by cracks and cuts in pipes installed in the field equipment or the irrigation equipment failure, and the second aerial image does not include the first aerial image of the phenomenon that results from the fault in the field equipment.

8. The field management apparatus according to claim 7, wherein, in the (a), a classifier for identifying the aerial image of the phenomenon that results from the fault in the field equipment and the aerial image of the phenomenon that results from normal operation of the field equipment is created by deep learning, and the created classifier is set as the learning model.

9. The field management method according to claim 7, wherein the aerial image of the phenomenon that results from the fault in the field equipment, the aerial image of the phenomenon that results from normal operation of the field equipment and the third aerial image are visible images.

10. The field management method according to claim 7, wherein the aerial image of the phenomenon that results from the fault in the field equipment, the aerial image of the phenomenon that results from normal operation of the field equipment and the third aerial image are radar images.

11. The field management method according to claim 9, further comprising:

(e) generating a second learning model, by using a radar image of the phenomenon that results from the fault in the field equipment and a radar image of the phenomenon that results from normal operation of the field equipment to learn a feature amount of the radar image of the phenomenon that results from the fault in the field equipment, wherein, in the (b), a visible image of the target region taken from above and a radar image of the target region taken from above are acquired, in the (c):

the visible image of the target region taken from above acquired in the (b) is applied to the learning model generated in the (a), and a visible image of the phenomenon that results from the fault in the field equipment is specified in the visible image of the target region taken from above acquired in the (b), and the radar image of the target region taken from above acquired in the (b) is applied to the second learning model generated in the (e), and a radar image of the phenomenon that results from the fault in the field equipment is specified in the radar image of the target region taken from above acquired in the (b), and in the (d), the fault location of the field equipment in the target region is specified, based on the visible image of the phenomenon that results from the fault in the field equipment and the radar image of the phenomenon that results from the fault in the field equipment specified in the (c).

12. The field management method according to claim 7, further comprising:

(f) estimating a ground moisture amount of the target region, wherein, in the (d), the fault location of the field equipment in the target region is specified, based on the image of the phenomenon that results from the fault in the field equipment specified in the (c) and the ground moisture amount of the target region estimated in the (f).

13. A non-transitory computer readable recording medium that includes a program recorded thereon, the program including instructions that cause a computer to carry out:

(a) a step of generating a learning model for determining whether an aerial image of a phenomenon results from a fault in a field equipment by using first feature amounts extracted from a first aerial image of the phenomenon that results from the fault in field equipment and second feature amounts extracted from a second aerial image of the phenomenon that results from normal operation of the field equipment, wherein the field equipment is irrigation equipment;

(b) a step of acquiring an third aerial image of a target region;

(c) a step of applying the third aerial image to the learning model and specifying the aerial image of the phenomenon that results from the fault in the field equipment; and (d) a step of specifying a fault location of the field equipment in the target region, based on the aerial image of the phenomenon that results from the fault in the field equipment specified in the (c) step, wherein the first aerial image includes images showing one or more of water pooling, furrows collapsing in the field and changes in the growth of crops in the field caused by cracks and cuts in pipes installed in the field equipment or the irrigation equipment failure, and the second aerial image does not include the first aerial image of the phenomenon that results from the fault in the field equipment.

14. The non-transitory computer readable recording medium according to claim 13, wherein, in the (a) step, a classifier for identifying the aerial image of the phenomenon that results from the fault in the field equipment and the aerial image of the phenomenon that results from normal operation of the field equipment is created by deep learning, and the created classifier is set as the learning model.

15. The non-transitory computer readable recording medium according to claim 13, wherein the aerial image of the phenomenon that results from the fault in the field equipment, the aerial image of the phenomenon that results from normal operation of the field equipment and the third aerial image are visible images.

* * * * *